US011865222B2

(12) United States Patent
Baker

(10) Patent No.: US 11,865,222 B2
(45) Date of Patent: Jan. 9, 2024

(54) MULTIMODAL AUTOMATED DISINFECTING SYSTEM

(71) Applicant: GMA International Services, Inc., Davie, FL (US)

(72) Inventor: Robert Baker, Marianna, FL (US)

(73) Assignee: GMA International Services, Inc., Davie, FL (US)

( * ) Notice: Subject to any disclaimer, the term of this patent is extended or adjusted under 35 U.S.C. 154(b) by 32 days.

(21) Appl. No.: 17/774,726

(22) PCT Filed: Apr. 9, 2021

(86) PCT No.: PCT/US2021/026537
§ 371 (c)(1),
(2) Date: May 5, 2022

(87) PCT Pub. No.: WO2021/211365
PCT Pub. Date: Oct. 21, 2021

(65) Prior Publication Data
US 2023/0024161 A1    Jan. 26, 2023

Related U.S. Application Data

(60) Provisional application No. 63/043,067, filed on Jun. 23, 2020, provisional application No. 63/010,618, filed on Apr. 15, 2020.

(51) Int. Cl.
*A61L 2/22* (2006.01)
*A61L 2/24* (2006.01)

(52) U.S. Cl.
CPC .................. *A61L 2/24* (2013.01); *A61L 2/22* (2013.01); *A61L 2202/121* (2013.01); *A61L 2202/122* (2013.01); *A61L 2202/14* (2013.01); *A61L 2202/15* (2013.01); *A61L 2202/25* (2013.01)

(58) Field of Classification Search
CPC ........ A61L 2/24; A61L 2/22; A61L 2202/121; A61L 2202/122; A61L 2202/14; A61L 2202/15; A61L 2202/25
USPC ....................................................... 422/105
See application file for complete search history.

(56) References Cited

U.S. PATENT DOCUMENTS

| 2004/0238019 A1 | 12/2004 | Kuenkel |
| 2005/0217700 A1 | 10/2005 | Davis et al. |
| 2006/0140703 A1 | 6/2006 | Sacks |
| 2007/0016328 A1 | 1/2007 | Ziegler et al. |
| 2010/0294915 A1 | 11/2010 | Williams et al. |
| 2010/0307544 A1 | 12/2010 | Lele et al. |

(Continued)

*Primary Examiner* — Huy Tram Nguyen
(74) *Attorney, Agent, or Firm* — Fleit Intellectual Property Law; Jon Gibbons

(57) ABSTRACT

A system and method are defined for disinfection of the structure, contents and included air in large volume enclosures such as mass transit vehicles, transport containers, warehouses, and retail sales or gathering locations to reduce the risk of transmission of contagious biological agents, particularly bacterial and viral agents. Various embodiments provide effective sanitizing actions accommodating differing local circumstances and obstacles. Safety interlock mechanisms, procedural steps and communications means ensure safe operations around humans and animals. The system includes a method for measuring environmental conditions to ensure a safe re-entry state.

19 Claims, 17 Drawing Sheets

(56) References Cited

U.S. PATENT DOCUMENTS

| | | |
|---|---|---|
| 2013/0216438 A1 | 8/2013 | Hill et al. |
| 2015/0064066 A1 | 3/2015 | Schwartz et al. |
| 2017/0210353 A1 | 7/2017 | Stauffer et al. |
| 2018/0200661 A1 | 7/2018 | Pui et al. |
| 2018/0313617 A1* | 11/2018 | Harris .................... F24F 11/83 |
| 2020/0086338 A1 | 3/2020 | Hogan et al. |

* cited by examiner

MULTIMODAL AUTOMATED DISINFECTING SYSTEM

CROSS-REFERENCE TO RELATED APPLICATIONS

This application claims priority from and is related to each of the following prior applications U.S. Provisional Application No. 63/010,618, filed Apr. 15, 2020 and U.S. Provisional Application No. 63/043,067, filed Jun. 23, 2020. Each of these prior applications, including the entirety of the written description and drawing figures, are hereby incorporated into the present application by reference in their entirety.

FIELD OF THE INVENTION

The present invention relates to the field of disinfecting as applied to the structure, contents and included air in large volume enclosed spaces such as mass transit vehicles, restaurants, transport containers, warehouses, and retail sales or gathering locations to reduce the risk of transmission of contagious biological agents, particularly bacterial and viral agents.

BACKGROUND OF THE INVENTION

The pandemic of 2020 reminded the world that modern societies are not immune to disease and the potential spread of pathogens worldwide. Effects on various nations included shortages of drugs, protective equipment, and medical devices needed for treatment. Impact was also felt through the reduction of travel to attempt to minimize the spread. Despite the many measures employed, Covid-19 and later variants were transmitted by breathing in or ingesting virus particles, being in close physical contact with people, and touching surfaces that were contaminated with the virus. Since its arrival, the virus has been detected in and on modern mass transit vehicles and stations, cargo transport containers, retail and exercise locations, and entertainment venues.

The variety of transmission methods indicates that different approaches are necessary to reach virus particles where they are found. Airborne pathogens are completely unaffected by manual surface wiping, for example. Conversely, air filtration has no effect on surface contamination. It is important to match the disinfection approach to the infection method, and that often involves multiple tactics.

Numerous techniques and types of equipment have been used to provide disinfection services. Surfaces can be cleaned manually using chlorine-based or other chemical solutions. Some of these solutions are also suitable for manual spraying and fogging using hand-held devices. Ultraviolet (UV) light in the UV-A, UV-B and UV-C ranges are currently in use for disinfection in enclosed spaces not inhabited by living beings at time of treatment. There are also systems that use UV light to produce hydroxyl radicals that bond with and kill certain pathogens. Stationary or cart-based fogging machines have also been developed for moving around in places needing disinfection.

Among these tools and methods, there is an enhanced benefit to deploying automated systems. This is evident in the reduction of exposure of people to disinfectants and the lower cost of equipment amortized over time versus the cost of manual cleaning crews. Labor costs ordinarily exceed simple hourly wages when various employee benefits are added.

Unfortunately, there is a high level of variability in cleaning/disinfecting performance by people carrying out manual cleaning. Cleaning effectiveness will vary from person to person and for individuals on a daily basis. Repeatability of effective performance is hard to achieve for mundane tasks such as manual cleaning and disinfecting.

For Covid-19 and other pathogens, the need was thus uncovered for effective automated systems and methods for eliminating or reducing infectious agents in large enclosed areas to reduce the risk of human transmission.

BRIEF SUMMARY

The system and method of the present application meet the needs of infectious agent control for enclosed spaces. This is achieved by employing various technologies and techniques to safely distribute disinfecting solutions through large volume, limited access spaces. The components and methods described hereinafter are applicable to several kinds of enclosed spaces. Examples include passenger-bearing mass transit vehicles, transport containers with various types of cargo or packages within, warehouses or storage depots. Further examples include retail sales or gathering locations such as stores, movie theaters, restaurants, banks, hotels, offices, sports arenas, and fitness centers, among others.

Elements and techniques of the present application are designed to deal with airborne pathogens, odors, surface contamination, and pathogens in hidden spaces. The multiple modes of this system are various modes of initiating disinfecting actions coupled with different modes of disinfectant deployment. The system accomplishes these things by dispersing one or more types of disinfectant fluid mists or fogs for different lengths of time using alternative nozzles or fluid dispersal outlets with or without fans. The system achieves different modes of activation through a variety of control initiating mechanisms. The combined and various dispersal methods ensure the capability of reaching infectious agent particles in the spaces and on the surfaces where they may exist after contact with an infected person or object. Fog, mist and spray dispersal is achieved by pumping disinfectant fluids under pressure through a variety of nozzle types or fluid dispersal outlets distributed within an area to be treated. This is typically accomplished through pumps, manifolds, pipes, valves and nozzles in fluid communications with each other. A high pressure fogging system will push fog particles for dozens of feet from each source nozzle. Another technique for fog dispersal is by spreading a mist or fog in that space with strategically placed fans. Yet another technique for fog dispersal is through activating HVAC systems serving the space being treated.

The large volume spaces addressed with the present application are those involved with any living organism (plants, animals, bacterial and viruses) presence and contact, creating the possibility of transmission of illnesses in those spaces. The prospect of living organisms presence introduces the requirement for safe disinfection methods, fluids and tools. Advantages of the present application are the inclusion of automated safety interlocks, presence detectors and activation alarms. A further advantage is a method for including manual confirmation of spaces to be free of specific living organisms, such as humans or animals.

The system and method of the present application also disclose multiple activation methods for the disinfection equipment. One such method is a remote activation and discontinuation mechanism for use by a central authority. An additional method is local activation at the site being disinfected. A third method involves prior scheduling using a real-time clock and calendar to drive activation. A risk identified with using remote controls is that they sometimes introduce an avenue for external tampering with control signals. Innovations in the present application take advantage of a plurality of safety interlocks to ensure that living organisms are not inadvertently or intentionally exposed. In addition, the overall system includes techniques for fail-safe operation using localized processing to resist efforts at tampering through outside channels.

Dispersal control is another advantage disclosed herein that directs effective distribution of mist or fog into large volumes. Monitoring movement of a disinfecting fog dynamically ensures removal or evaporation of disinfectant fluid after treatment so as to allow the safe return of people or other living organisms to the sanitized space. The addition of this capability is another safety technique employed in the present application.

The system of the present application provides the mechanisms for generating "dry fogs", "wet fogs" and "mists." Dry fogs are characterized by smaller particle size with lower mass, while wet fogs have larger and heavier fog particles. Mists have even larger particles better described as "droplets." Dry fogs are more effective at interacting with airborne virus particles, while wet fogs and mists tend to fall and reach virus particles on surfaces.

The tools and methods of the present application operate in multiple modes separately and in concert to provide an effective and safe system and method for automating the disinfection of large volume areas or vehicles.

In one example, a disinfecting system includes a controller for controlling the operation of a pump, a reservoir for holding disinfection liquid, and a manifold in fluid communications with the pump and the reservoir. The manifold distributes the disinfection liquid which the pump has pressurized to a set of nozzles. The controller turns on the operation of the pump based on one of at least three modes of initiation: 1) a stored schedule, or 2) input to a rule-based engine, or 3) a manual input from an operator. Inputs to the rule-based engine include one or more of the geographic position of the disinfecting system, temperature and humidity in a defined area, amount of disinfecting liquid available, safety interlocks are satisfied, occupancy sensors indicate no presences of an animal or human in a defined area with the disinfecting system, a quantity of animals or humans or a number of visits, including repeat visits of animals or humans in the defined area over a given period of time. In one embodiment, the disinfecting system is installed on a bus, a tram, a shipping container, a taxi, a van, a train, a subway, an automated people mover, an autonomous vehicle, a private mass-transit system, or a public mass-transit system.

In another example, a disinfecting system includes a controller for controlling operation of a pump, a reservoir for holding disinfection liquid, a manifold in fluid communications to the pump and the reservoir, and the manifold. The manifold distributes the disinfection liquid which the pump has pressurized to a set of nozzles. The disinfecting system further includes a first set of humidity sensors positioned at a first distance from the set of nozzles in a predefined space and a second set of humidity sensors positioned at a second distance from the set of nozzles. In response to a second definable humidity level that is above a second definable threshold as measured at the second set of humidity sensors, the controller controls the operation of the pump to run. In response to a first definable humidity level that is measured as below a second definable threshold as measured at the first set of humidity sensors, the controller provides a notification that it is safe for animals or humans to enter the predefined space. In one embodiment, the controller turns on the pump based on one of at least three modes of initiation: 1) a stored schedule, or 2) input to a rule-based engine, or 3) a manual input from an operator, and the rule-based engine includes a geolocation system to provide a geographic position of the disinfecting system. Inputs to the rule-based engine include one or more of geographic position of the disinfecting system, temperature and humidity in a defined area, amount of disinfecting liquid available, safety interlocks are satisfied, occupancy sensors indicate no presence of an animal or human in a defined area with the disinfecting system, a quantity of animals or humans or a number of visits, including repeat visits of animals or humans in the defined area over a given period of time. In one embodiment, the disinfecting system is installed on a bus, a tram, a shipping container, a taxi, a van, a train, a subway, an automated people mover, an autonomous vehicle, a private mass-transit system, or a public mass-transit system.

The disinfecting system may further include an auxiliary reservoir with an auxiliary reservoir pump in fluid communications with the reservoir. The disinfecting system includes a sensor to measure the amount of liquid in the reservoir. Auxiliary pump controller turns on the auxiliary reservoir pump to fill the reservoir until a predetermined level is measured.

In another example, a disinfecting system includes a controller for controlling operation of a pump and a reservoir for holding disinfection liquid. The disinfecting system further includes a manifold in fluid communications to the pump and the reservoir, and the disinfection liquid which the pump has pressurized to produce a pressurized disinfection liquid which is distributed by the manifold to a first set of nozzles with a first aperture size and a second set of nozzles with a second aperture size. The first set of nozzles modifies and ejects the pressurized disinfection liquid as a dry fog with a fluid particle size up to 15 microns and the second set of nozzles modifies and ejects the pressurized disinfection liquid as a wet fog with a fluid particle size between 30 to 70 microns. In one example, the disinfecting system may include a third set of nozzles for modifying and ejecting the pressurized disinfection liquid as a mist fog with a fluid particle size between 100 to 300 microns, and the third set of nozzles is in fluid communications with the pump. Typically the disinfecting system may include a valve for controlling the distribution of pressurized disinfection liquid to the first set of nozzles, the second set of nozzles or both. The valve is in fluid communications between the manifold and one of the first set of nozzles, the second set of nozzles, or both. Further, the disinfecting system may include a valve actuator communicatively coupled to the controller for opening and closing the valve.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

Figure 1:
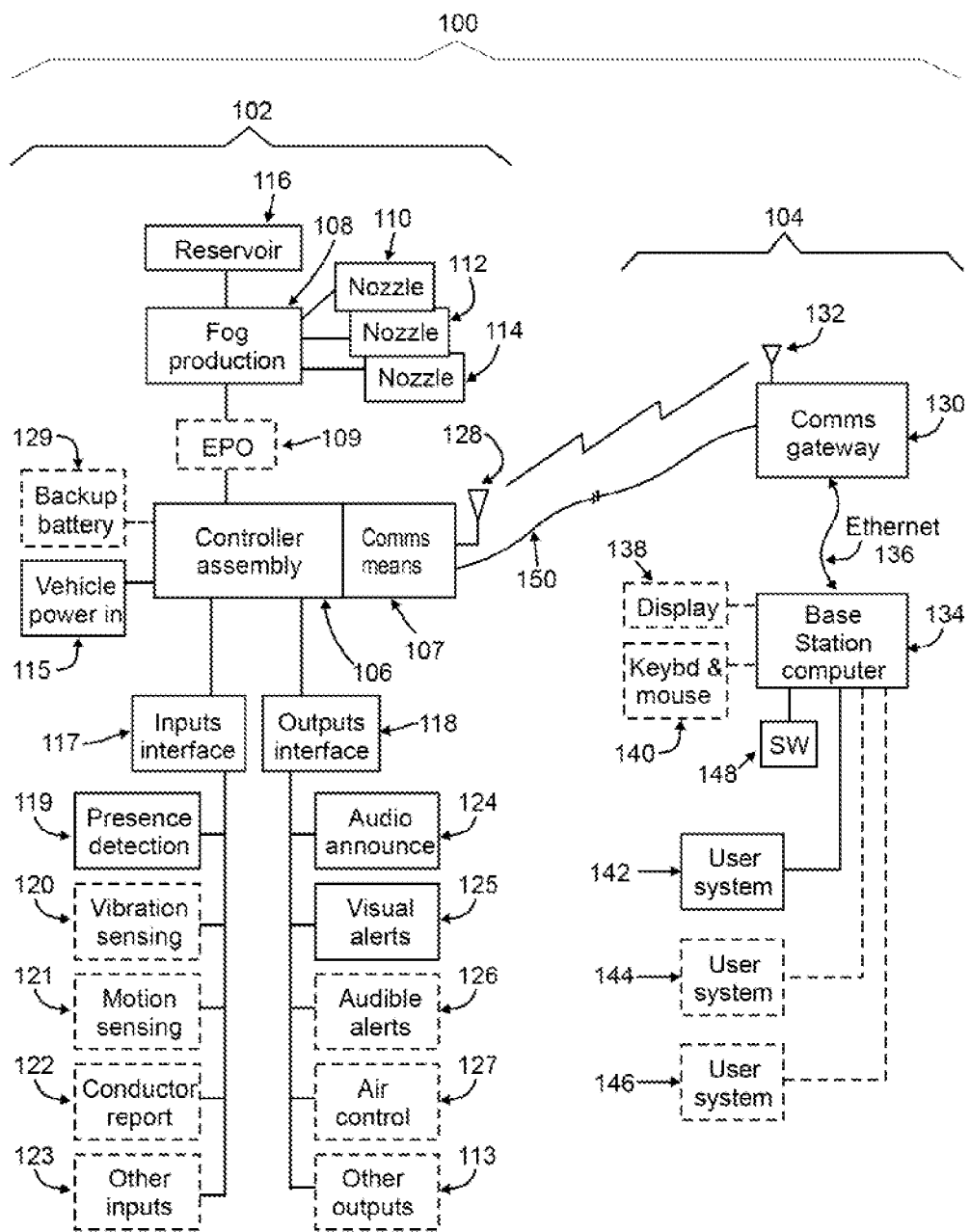
FIG. 1 is a block diagram of one embodiment of a complete representative disinfection system according to the present application that is applicable across a variety of supported environments.

In the following detailed description, specific examples are discussed with reference to the accompanying drawings that form a part hereof. These examples describe the system and method in sufficient detail to enable those skilled in the associated arts to practice the invention. It should be understood that these are examples only, and they should not be taken as limiting. Other examples may also be practiced that are consistent with the spirit and intention of the present system and method and apparent to those skilled in the associated arts, and the scope is defined by the appended claims and their equivalents.

Non-Limiting Terminology

The terms "a" or "an", as used herein, are defined as one or more than one. The term plurality, as used herein, is defined as two or more than two. The term another, as used herein, is defined as at least a second or more.

The term "adapted to" describes hardware, software or a combination of hardware and software that is capable of, able to accommodate, to make, or that is suitable to carry out a given function.

The term "and" in the phrase "one of A, B, and C" means either A or B or C or any combination of A, B, and C.

The term "controller", as used herein, means an electronic system that manages and commands the disinfection system.

The term "configured to", as used herein, describes hardware, software or a combination of hardware and software that is adapted to, set up, arranged, built, composed, constructed, designed or that has any combination of these characteristics to carry out a given function.

The term "coupled", as used herein, is defined as "connected" although not necessarily directly, and not necessarily mechanically.

The term "defined area" or "predefined space" or "enclosed space", as used herein, is any section or portion or floor of a bus, a tram, a shipping container, a taxi, a van, a train, a subway, an automated people mover, an autonomous vehicle, a private mass-transit system, or a public mass-transit system.

The term "disinfection liquid" means any solution that can clean and disinfect air and surfaces to neutralize harmful pathogens and/or unpleasant odors. Common commercially available solutions include chlorine-dioxide and hydrogen peroxide, but other solutions are possible.

The term "geolocation system" is any system for determining a geographic position of an object, such as a disinfecting system, including global position systems (GPS), cellular position systems, Wi-Fi positioning systems, Internet Position systems, and other positioning systems.

The terms "including" and "having", as used herein, are defined as comprising (i.e., open language).

The term "manifold" is a mechanism or device designed to distribute liquid to distribution lines which typically terminate with one or more nozzles.

The term "nozzle" is a device designed to control the direction or characteristics of a fluid flow, typically by increasing velocity as it exits an enclosed chamber or pipe. The term is used interchangeably with "fluid dispersal outlet" and is equivalent in functions and performance defined herein.

The term "pump" is a device that moves liquids, such as disinfection liquid, by mechanical action either by direct lift, displacement, or gravity. Pumps operate via many energy sources, including manual operation, electricity, engines, pneumatic, or wind power, and come in many sizes, from microscopic for use in medical applications, to large industrial pumps.

The term "sensor" is a device that detects changes in an environment or events, such as temperature, humidity, pressure, vibration, chemical properties, liquid levels, images, acoustic, sound, fluid flow, moisture, weather, electric current, proximity, presence, and other detectable properties.

The term "stored schedule" consists of a list of times at which possible tasks, events, or actions are intended to take place, or of a sequence of events in the chronological order in which such things are intended to take place.

The term "valve" is a device that regulates, directs or controls the flow of a fluid by opening, closing, or partially obstructing various passageways.

The term "valve actuator" is a mechanism for opening and closing a valve.

The term "wireless" or "wireless communication" is the electromagnetic transfer of information between two or more points that do not use an electrical conductor as a medium by which to perform the transfer. The most common wireless technologies use radio waves. With radio waves, intended distances can be short, such as a few meters for Bluetooth, or many kilometers for satellite communications.

Overview

A system and method is described herein for disinfecting the contents and included air in large volume enclosures such as mass transit vehicles, transport containers, warehouses, and retail sales or gathering locations. Other intended large volume enclosures include entertainment venues, fitness centers, offices and office buildings, movies theaters, schools, and hotels, among others. The primary purpose of such disinfecting systems and methods is to reduce the risk of transmission of contagious agents, particularly bacterial and viral agents. A secondary purpose is to freshen the air through the introduction of odor-neutralizing chemicals or fragrances. Various configurations of system and subsystem components facilitate optimization of functions for system deployment in assorted environments and applications. The following drawings are provided to illustrate details and a subset of possible configurable embodiments for the purposes of illustrating principles of operation.

FIG. 1 is a block diagram that depicts one embodiment of a representative disinfection system 100 that is applicable for both stationary and mobile environments. This is an automated system that is capable of operating in various modes for safely producing and dispensing disinfecting fluid particles in large volume enclosures. The system is made up of a fog producing subsystem 102 and a remote control and command subsystem 104. Some embodiments of the system provide services without the use of a remote control and command subsystem 104. Fogging parameters are programmed into the fog producing subsystem 102 through direct connections or short range communications means. FIG. 1 includes the remote control and command components 104 to illustrate the various modes of operation. The fog producing subsystem 102 is comprised of a means for producing fog particles, input and sensing interfaces, and output and control interfaces. The means for producing fog include various nozzles and outlets with various sized orifices for producing different particle sizes, plus a means for distributing the disinfecting fluid. The modes of operation, as explained later, include the capability of producing and dispensing fluid particles in various sizes selected from a group consisting of 5-15 micron dry fogs, 30-70 micron wet fogs, 100-300 micron mists and 350+ micron sprays. Different sized particles have different levels of effectiveness for various types of infectious biological agents that are either airborne or resident on surfaces.

For the purposes of illustration, the term "local" is being used to represent the deployed fog-producing portion of the system in an example transit implementation. Other terms such as "on-board" or "in-enclosure" are readily substituted for "local" to identify the components that are located within a large volume enclosure that is being sanitized. The local subsystem 102 is deployed in locations that are being disinfected. In this embodiment, spaces being disinfected are presumed to be managed by a centralized authority. This is not a limiting factor but is used to illustrate an example of a deployed system. Remote control and command components 104 under the command of the centralized authority are housed separately, such as an authority's command center for a business or service operation. In this FIG. 1 embodiment, communications between a space's disinfecting system and the central authority's command center are shown as wireless since this example focuses on mobile platforms such as railcars or buses. However, communications are effectively carried out with wired connections for stationary spaces such as commercial business centers.

The FIG. 1 illustration depicts only a single disinfection system, but multiple of such systems are selectively in communication with a central control facility. In a passenger train implementation, a local subsystem 102 is installed in or on at least 1 car near or including the passenger cars. The remote control and command components 104 are preferably located in the centralized command center for a given transit authority. Using the passenger train example, the local subsystem 102 that performs the disinfecting actions includes various items. One such item is a controller assembly 106 with included communication means 107. In its simplest form, the local controller assembly is comprised of a processing means with associated memory, communications means, and input and output interfaces. The processing means is selected from a group of microcontrollers, microprocessors, VLSI, custom chip designs, timers, and other forms of digital logic components. Another item is a fog production subsystem 108 to which manifolds with nozzles 110, 112 and 114 are connected to disperse the fog. There is also a corresponding disinfectant solution reservoir 116. An optional EPO or "Emergency Power Off" element 109 is available for authorities that want the freedom to quickly disable a fogging event in process. Although only one device is shown, one or more such EPO devices are selectively installed in key locations in a space. EPO devices are ordinarily used to stop a process in the event of an emergency situation.

In this embodiment, communications exchanges take place over an appropriate RF antenna 128 for the given communication means. Power to operate the local systems is selectively provided by the vehicle's power source 115. An optional backup battery 129 provides power to the controller assembly for limited communication and sensing activities in the absence of vehicle power, such as in layover periods. In embodiments involving stationary locations, the power is supplied through standard outlets connected to the prevailing power grid or self-generated power sources.

The controller assembly 106 has numerous associated devices electrically connected through an interface for inputs 117, such as inputs from one or more sensors. Typical input devices and sensors include presence detection devices 119, vibration and motion sensors 120 and 121 respectively, relative humidity and temperature (RHT) sensors (not separately shown), and others. A vibration sensor 120 is optionally employed to determine whether there is any activity on a vehicle. For example, such a sensor can detect the vibrations of a person walking through a vehicle, indicating the presence of a person on board, a contraindication to fogging. A motion sensor 121 operates by detection of minute changes in orientation. Thus, a motion sensor detects the bumps and swaying of a vehicle in motion, another potential restriction against fogging.

Presence detection devices 119 selectively incorporate infrared (IR), ultrasonic, visual sensors or other means to determine whether people or animals are present in the space. Each of these inputs supports safety interlocks to prevent operation of the disinfectant fluid dispersal system except when no people or animals are present.

GPS components are examples of another input 123 included with this embodiment. GPS components are alternatively placed on a controller assembly or an extended interface. Location data is captured from such components and transmitted to the remote control and command components 104 for processing. Through calculations of position over time, the base station computer 134 and its associated software 148 are able to determine whether a train is moving or stationary. Since vehicle movement is associated with passenger travel at service times, fogging events are potentially contraindicated in certain cases of movement. GPS location data is also optionally used to determine that a train is at a designated location at which no passengers should be on board, such as a maintenance yard. The information provided by GPS data is therefore available to a rule-based engine for appropriateness of conducting fogging with that equipment. Knowledge of locations through GPS allows establishment of geofences to limit fogging locations to where passengers should not be on board. GPS information is selectively processed in the controller assembly 106 or alternatively transmitted to a base station computer that is part of a remote control and command subsystem 104. If not processed in the base station computer 134, the GPS data is optionally retained in the controller assembly 106 as an input to a safety interlock.

Yet another example of an input device is a touch panel or pushbutton array used to select different zones for disinfecting in systems with multiple fogging zones. Various types of input devices are typically employed for making selections on computer based systems. The type of input device ordinarily employed for interfacing with processing means is not to be seen as a limiting factor in this application.

As another aspect of a passenger safety provision, as part of a disinfection process, a transit authority often requires a conductor or staff member to verify safe operating conditions. Such a validation selectively includes a walk through a stationary vehicle that is preparing for disinfection. Upon verifying that no one is present, the staff member reports the status to the command center and exits the vehicle, in no required order. The conductor report 122 is optionally completed by actuating a key switch on the train. The switch is connected through the inputs interface 117 to the controller assembly 106, which is able to transmit the information through the communications means 107 to the base station computer 134. Alternative mechanisms not involving wired connections include calling in to a command center by phone or reporting the vehicle's status in person. These would obviously not be carried out through the inputs interface 117. A conductor report 122 is also alternatively completed using wireless communications, an example of which is an app for a cell phone. The method of conductor reporting is not intended to be limiting to the process. The conductor report 122 provides an affirmative and additional safety interlock to prevent human exposure to disinfection chemicals.

The controller assembly 106 also has control functions that are addressed through an outputs interface 118. One such output is an audio announcement subsystem 124 that warns of a pending disinfection in the space. Another example output is a strobe light or other visual alert device 125 to let people know of a disinfection that is pending or in progress. Different visual alerts are possible for different stages of the disinfection process. Audible alert devices 126 include beepers, buzzers or other audio devices used to notify people of the disinfection process. In addition, the controller assembly 106 controls optional air movement devices through air control relays 127. Such air movement devices selectively include fans or the vehicle HVAC systems. These air movement devices help distribute the disinfecting fog and support evaporation from surfaces after treatment as appropriate for a given treatment regimen. Examples of other outputs 113 include devices for controlling aspects of the disinfection process, such as one or more fluid control valves and valve actuators (not separately shown) for directing disinfecting fluids to a specific vehicle in a larger train set or zone within a stationary space.

Continuing with FIG. 1, the remote control and command components 104 include a communications gateway or receiver 130 with associated antenna 132 for corresponding with one or more related local subsystems 102. RF communications are most beneficial for local subsystems 102 housed on mobile platforms like train cars or buses. An Ethernet or other local wired data connection 136 connects the communications gateway 130 with a base station computer 134 and its associated software 148. This computer 134 optionally has its own independent display 138 and keyboard plus mouse I/O 140. Alternatively, the base station computer 134 operates in networked mode and is housed in an equipment area. This computer 134 is accessed through one or more authorized user systems 142, 144, 146 from local or remote terminals. Access is alternatively configured for both local individual and multiple network-accessible terminal points in various locations. Software 148 running on the base station computer 134 facilitates command and control and data collection functions at the central control location. Such software is optionally employed to handle databases of information associated with the disinfection equipment and processes. For example, such software is optionally constructed to manage fogging event databases, maintenance databases, failure logs, equipment configuration data, fogging schedules, and more. Software 148 is also a preferred tool for carrying out communication with management and staff by collecting and analyzing data and forwarding reports to selected individuals. Reports variously take the form of email, SMS text messages, online screens, or printed reports as preferred by the governing authority. Depending on the preferred configuration, the base station computer 134 is alternatively placed in an employee's workspace or housed in a data closet with access through electronic connectivity.

Since not all local subsystems are housed on mobile platforms, wired communications are also effective for conveying data between the stationary fog-producing subsystems and the remote control and command computer. A wired connection 150 such as Ethernet is shown as an alternative communications method. Such a wire connection is typically employed for communications between stationary local and remote subsystems.

In carrying out its purpose in FIG. 1, the local subsystem 102 manages and conducts the large volume disinfection through dispersal of disinfecting solution mists and fogs. There are numerous commercially-available disinfecting fluids, chemicals, and mixtures that are effective for this function.

The physical properties of aerosol particles indicate different dispersion effects related to the particle sizes. Wet fogs generally have a dispersion pattern in the direction of the pressurized propelling force and downward, since the particles have a larger mass that is affected by gravity in normal air. Still larger particles like mists and sprays are capable of being propelled farther, but they are heavier and therefore tend to fall faster. The smaller particle sizes of dry fogs, on the other hand, allow selectable buoyancy of particles in the air. For example, neutral-buoyancy dry fog particles float in the air and follow almost-imperceptible air currents in the absence of forced air movement. This is similar to the behavior of visible smoke drifting in the breeze. Depending on the constituent fluids formulated in a fog-producing disinfecting solution, dry fogs are designed to either rise (lighter than air), fall (heavier than air) or simply float on air currents. The lightweight behavior of dry fogs allows penetration of disinfectants into cracks, crevices and other hard-to-reach spaces for more thorough sanitizing. It should be noted that disinfecting fogs affect airborne odor particles as well as infectious agents, sanitizing the air and neutralizing odors at the same time.

To achieve the small particle size of dry fogs without heating the liquid disinfectants, liquids are atomized by forcing them through small nozzles at high pressure. For example, liquid water pushed at 1,000 psi through a 0.004" orifice in a nozzle is capable of producing a dry fog. Larger orifices in nozzles are capable of producing a wet fog with larger particles at the same high pressure. Sprays are generally produced with lower pressures in the 100-300 psi range with various sized nozzles.

The system of the present application is designed to produce both dry fogs, wet fogs and mists through the implementation of different sized nozzles operating at high pressure. The dry fog particles are effective for disinfecting airborne virus particles and for penetrating into cracks and crevices where pathogens may travel. Such dry fog particles also reach areas where moisture accumulates, and appropriate disinfectant solutions are also effective against molds and mildew. The system of the present application also produces wet fog particles, which are heavier and prone to falling onto surfaces faster than dry fog particles. A wet fog ordinarily settles on horizontal and some vertical surfaces, wetting the surfaces for a period of time. Persistence of moisture on a surface defines the "dwell times" that are necessary for a given disinfectant to kill various pathogens or bacteria. Dwell times are characteristically identified by the EPA for solutions claiming disinfection properties. Different dwell times are usually required for different pathogens for each type of disinfectant fluid.

The system of the present application is alternatively capable of generating wet fogs by super-saturating the air with excess dry fog particles. As smaller dry fog particles more densely fill a given volume of air, their interaction causes particles sizes to grow through combination, resulting in wet fog. As noted earlier, wet fogs are useful for moistening surfaces on which pathogens may have landed from human contact, sneezing, or coughing. The capability of this system to attack infectious agents in both airborne settings as well as on surfaces is of critical value as the science of Covid-19 transmission continues to develop. The lack of a conclusive transmission mechanism at this time demonstrates the importance of this multimodal approach to the application of disinfectants.

Referring again to FIG. 1, the controller assembly 106 handles the control and interfacing responsibilities on a local basis at the disinfection sites. The processing means on the controller assembly 106 is selected from a group of microcontrollers, microprocessors, VLSI, custom chip designs, timers, and other forms of digital logic components. One of more of these control mechanisms selectively operates to conduct a predetermined disinfection process. The system of the present application thus operates in one of several modes to perform this process. One mode of operation is activation of a timer by a predetermined schedule locally recorded in the controller assembly 106. A second mode of operation is through remote and local inputs to a rule-based engine running on processing means on the controller assembly 106. A third mode of operation is dynamic activation through a manual input mechanism such as a key switch or push button. Alternatively, manual inputs are optionally provided through a wireless mechanism such as a phone application if appropriate hardware and software are included in the configuration. Each of these modes starts a timer that runs for a predetermined duration that is designed to match the disinfection needs of the space being treated for the specific disinfectant solution being employed.

In the first mode, a schedule is maintained in memory associated with the processing means of the local controller assembly 106. The schedule is conventionally loaded by an initial wired connection, by short range wireless connections, or through the communication means 107 from the base station computer 134. There is no technical limitation on when or how the schedule is loaded. However, management authorities often establish organizational protocols to govern how schedules are loaded or changed and by whom. For security purposes, schedules are optionally protected for any changes not performed under defined conditions.

In a second alternate mode of operation, a rule-based engine running on processing means on the controller assembly 106 determines suitable conditions for conducting a disinfection by evaluating one or more of various inputs. Examples of such inputs are location, absence of human presence as detected at the disinfection site, lack of vibration, lack of motion, confirmation of no people present through a conductor report, sufficient quantities of disinfectant fluid in the reservoir, on/off status of HVAC, and appropriate relative humidity and temperature. Appropriate inputs are specified for a given type of installation to meet the objectives of a disinfection process tuned to a given setting. One or more of the inputs is selectively evaluated by the rule-based engine in order to initiate and carry out a fogging event.

A third alternate mode of operation is dynamic local control initiated by a local switch of some kind. In this mode, a fogging event is started at will by a local authorized staff person or manager. The type of local switch is one of many conventional types, and this is not a limiting factor.

Evaluation of conditions from various inputs is not limited to an activation mechanism through a rule-based engine. Conditional continuation of a disinfection event based on various inputs is consistent with the principles of the present application and expressly anticipated. For example, it is expected that a schedule-initiated event will perform safety interlock checks to ensure suitable operating parameters. The number and extent of such checks is part of a custom system definition that suits a given client.

Regardless of starting mechanism, each of these modes initiates the timing of a known predetermined duration that has been calculated and tested to achieve effective disinfection for an enclosed space of specific parameters. The duration of an event can be curtailed through a safety interlock input or activation of an EPO, among other methods.

Other functions of the controller assembly 106 include the capability to transmit data such as disinfection start and stop times as conducted, loading updated schedules, logic or sequence modification for the rules-based engine, as well as receiving data, status and I/O inputs from the installed vehicle.

Figure 2:
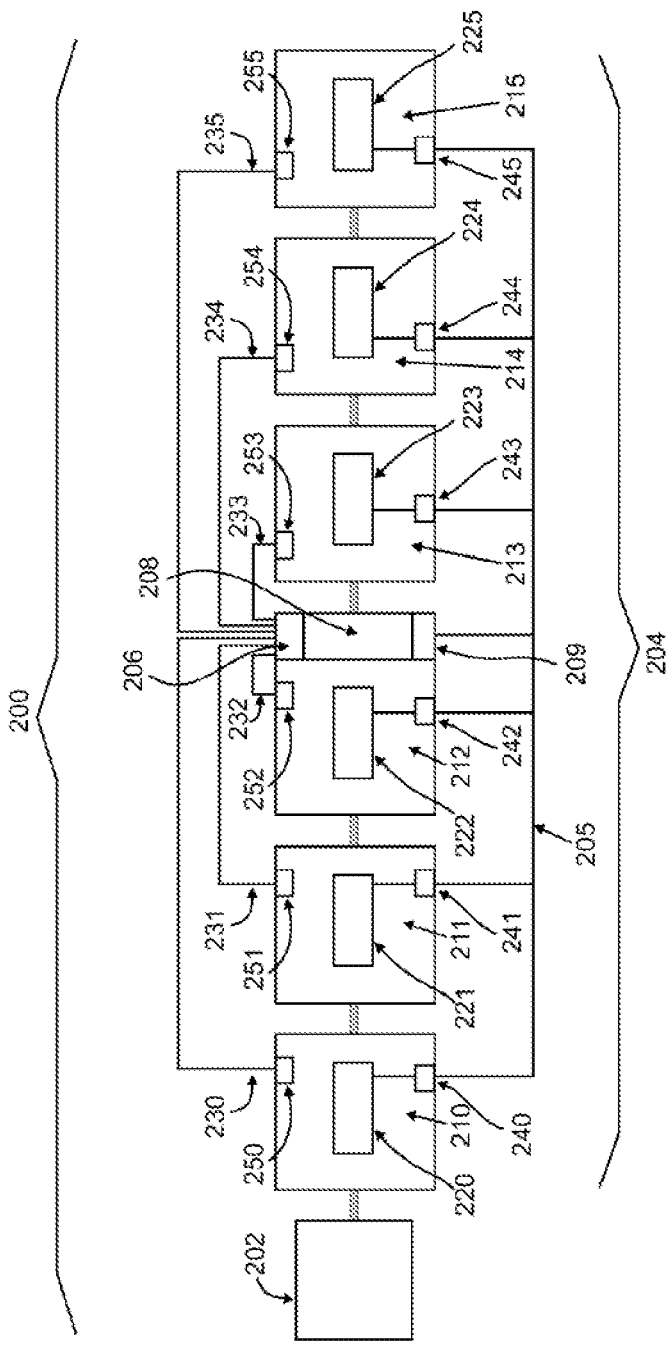
FIG. 2 is an example of a passenger railcar embodiment with multiple cars showing one of many possible transit configurations.

FIG. 2 is an example of a train-length passenger railcar embodiment showing one of many possible configurations.

In this example embodiment, a complete commuter train 200 is made up of a locomotive 202 and a trainset 204 composed of 6 passenger railcars respectively numbered 210-215. A single controller assembly subsystem 206 in its housing is mounted in or on a vehicle near the middle of trainset 204. For the example shown, controller assembly subsystem 206 is affixed to the third passenger railcar 212 in the drawing. Located on or near the same car 212 is a disinfectant reservoir 208 that supplies disinfecting fluid to all the railcars in the trainset 204. The local disinfectant fog dispersing equipment is represented diagrammatically as items 220-225 and is installed in similar fashion in each of railcars 210-215, respectively. Electronic control lines 230-235 perform at least two functions. A first function is to connect with the various I/O devices, collectively numbered 250-255 in the respective railcars, to provide individual car safety interlock features, RHT data inputs, announcements and visual/audible alerts. One example of a sensor type is a vibration sensor for detecting motion of the vehicle or people inside the vehicle. An example of a visual alert is a strobe light. Output signals for activating status indicators (not shown) and air-movement devices (not shown) are also optionally included in these electronic control lines 230-235. Similarly, disinfectant fluid control valves 240-245 manage the flow of disinfecting fluids to the corresponding railcars 210-215 through a pump module 209 located near the reservoir 208. The pump module provides high pressure pumping involving pressurized fluids or air or both.

A single pipe or common tube for distributing fluids provides the means to serve all cars and allows individual car or group disinfection actions under control of the controller assembly subsystem 206. A single pipe or common tube is the fluid distribution means that are selected from a group consisting of pipes, hoses, manifolds, tubes and other fluid and air conveyances. Actuation of the pump module 209 is also managed by the controller assembly 206 based on choices of the operational authority in one of the modes consistent with the present application.

As illustrated in the example in FIG. 2, the system of the present application allows multiple control combinations among the railcars in a trainset through activation of the pump module 209. Based on the pump size defined for a given application environment, the system provides multiple operational configurations. One such configuration provides the capability of simultaneous disinfection actions among all cars at once. This is accomplished with a pump module large enough to handle all cars at on time. Another configuration performs individual disinfection operations in the connected cars. This is accomplished with a smaller pump module by sequencing the fogging events through the trainset car-by-car. Yet another configuration facilitates various combinations of cars being disinfected at one time based on circumstances. One example benefit of this capability is the freedom to selectively disinfect just one car in the trainset if an infected person has traveled on it. In contrast, it is potentially more convenient for a transit authority to schedule all cars to be disinfected at one time. As yet another example, if disinfecting fluid is running low in the centrally-located reservoir, a subset of the cars is selectively chosen for treatment at the authority's discretion. These and other benefits become apparent with additional consideration. The principles of this method and architecture are equally applicable to stationary installations as mentioned earlier.

Depending on the disinfecting fluid selected for the installation, an additional or auxiliary reservoir is optionally employed to hold a second disinfectant fluid type. For example, an airborne disinfectant dispersal solution is contained in one reservoir, while a surface-treating disinfectant solution is contained within another. The number of reservoirs and types of solutions are not to be considered a limitation of the system or methodology. Correspondingly, when more than one reservoir is employed, additional fluid supply lines (not shown in FIG. 2) are employed. Additional timers, program steps, or logic trees in rule-based engines are also alternatively included in a system to accomplish these objectives.

The term "supply lines" has been used for this description, but this should not be seen as limiting. Pipes, flexible hoses, metal braid covered tubes coupled together and in fluid communications with pumps, manifolds, valves, nozzles, or other means to convey and disperse fluids are suitable for implementation with this system and method.

Figure 3:
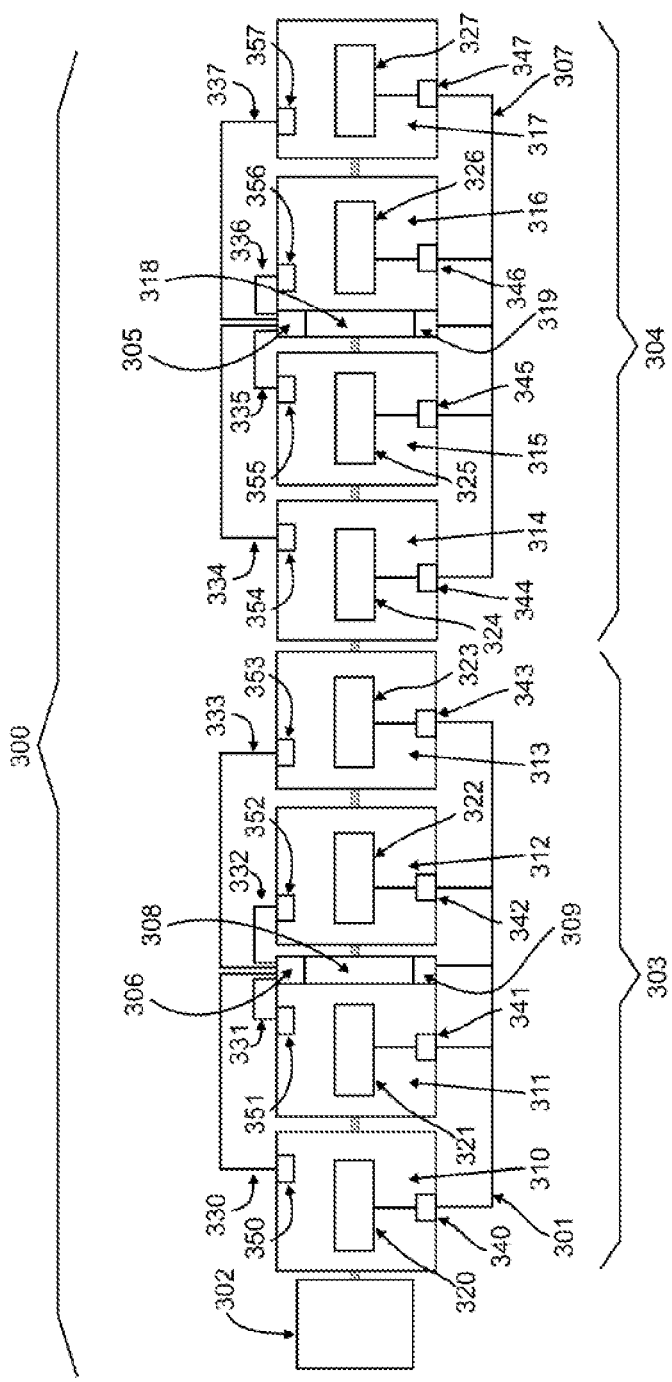
FIG. 3 illustrates an alternative embodiment of multiple large volume enclosure disinfection systems employed in a passenger rail trainset.

FIG. 3 illustrates an alternative embodiment of multiple large volume enclosure disinfection systems employed in a multi-car passenger rail trainset. In this FIG. 3 example embodiment, a complete commuter train 300 is made up of a locomotive 302 and two multi-car trainsets 303 and 304 consisting of 4 passenger railcars each. Trainset 303 is made up of railcars numbered 310-313, and trainset 304 is made up of railcars numbered 314-317. In this example embodiment, a single controller assembly subsystem 306 with its corresponding disinfectant fluid reservoir 308 manages sanitizing in trainset 303. Controller assembly subsystem 306 is arbitrarily centrally mounted on car 311 for purposes of illustration. A pump module 309 is located near the reservoir outlet to distribute disinfecting fluids to all cars in this trainset at one time or separately as desired. Fluids reach the fog-dispersing equipment 320-323 when transferred through a distribution line 301 to the fluid control valves 340-343 under direction of the controller assembly subsystem 306. Depending on the capacity of the pump module, one or more cars in the trainset are selectively fogged at one time. A car is fogged when fluids from the distribution line 301 are affirmatively passed through control valves 340-343 to each car's fog-dispersing equipment. As in other embodiments, fog-dispersing equipment consists of high pressure hoses, tubes, pipes or other suitable vessels, and appropriate nozzles for generating the fog.

Actuation of the pump module 309 is managed by the controller assembly subsystem 306 based on choices of the operational authority. The controller assembly subsystem 306, reservoir 308 and pump module 309 are alternatively mounted on any one of the other cars in 4-car trainset 303. Similar to trainset 303, a single controller assembly subsystem 305 with its corresponding disinfectant fluid reservoir 318 and pump module 319 manages sanitizing in trainset 304. Controller assembly subsystem 305 is arbitrarily mounted on car 316 for purposes of illustration but is reasonably mounted elsewhere in trainset 304. Fluids reach the fog-dispersing equipment 324-327 when transferred through a distribution line 307 to the fluid control valves 344-347 under direction of the controller assembly subsystem 305. Depending on the capacity of the pump module, one or more cars in the trainset are selectively fogged at one time. A car is fogged when fluids from the distribution line 307 are affirmatively passed through control valves 344-347 to each car's fog-dispersing equipment. Mounting locations are made in consideration of vehicle characteristics and maintenance or operational topics.

Additional control valves are also effective for controlling the distribution of fog in smaller spaces within a single car. For example, a conductor's or operator's cab or restroom are smaller volumes requiring less time applying fogs or mists. An auxiliary control valve in these spaces managed by the central controller assembly subsystem provides an optimized application of disinfectant fogs. Although not drawn, this feature is consistent with the principles of the present application.

Referring again to FIG. 3, the local disinfectant fluid dispersing equipment is installed similarly and represented diagrammatically as items 324-327 for trainset 304 cars 314-317, respectively. Electronic control lines 334-337 perform command and control functions for cars 314-317, respectively. Electronic control lines 330-337 perform at least two functions. A first function is to connect with the individual local I/O devices 350-357 in their respective railcars to provide personnel safety and operational information and alerts in individual cars. One example of these sensor types is a device for infrared detection of people, as provided in the other trainset. Output signals for activating status indicators (not shown) and air-movement devices (not shown) are also optionally included in these electronic control lines 330-337. As with other embodiments, depending on the disinfecting fluid selected for the installation, an additional reservoir is alternatively employed to hold a second disinfectant fluid type. In such a case, when more than one reservoir is employed per trainset, additional fluid supply lines (not shown in FIG. 3) are employed.

As illustrated previously in the example in FIG. 2, the system of the present application allows multiple control combinations among the railcars in a trainset at the direction of a controlling authority. This is also true for multi-trainset trains as illustrated in FIG. 3. The system provides the capability of various disinfection actions. One such action is the simultaneous disinfection of all cars or trainsets. Another such action is individual disinfection operations on a per-car basis. Further still, the system of the present application provides the capability of various combinations of cars being disinfected at one time based on circumstances. The benefits of selective disinfection exist for this illustration as previously explained.

For the distances that fluids are expected to travel as depicted in FIG. 2 and FIG. 3, hydraulic friction and other fluid-flow phenomena affect the passage of these fluids as they travel through the pipes or tube conveyances to the fluid dispersal devices or subsystems. The design of systems according to the methods of the present application accounts for the various dynamics to ensure effective fluid movement under normal operating conditions for a given application.

Figure 4:
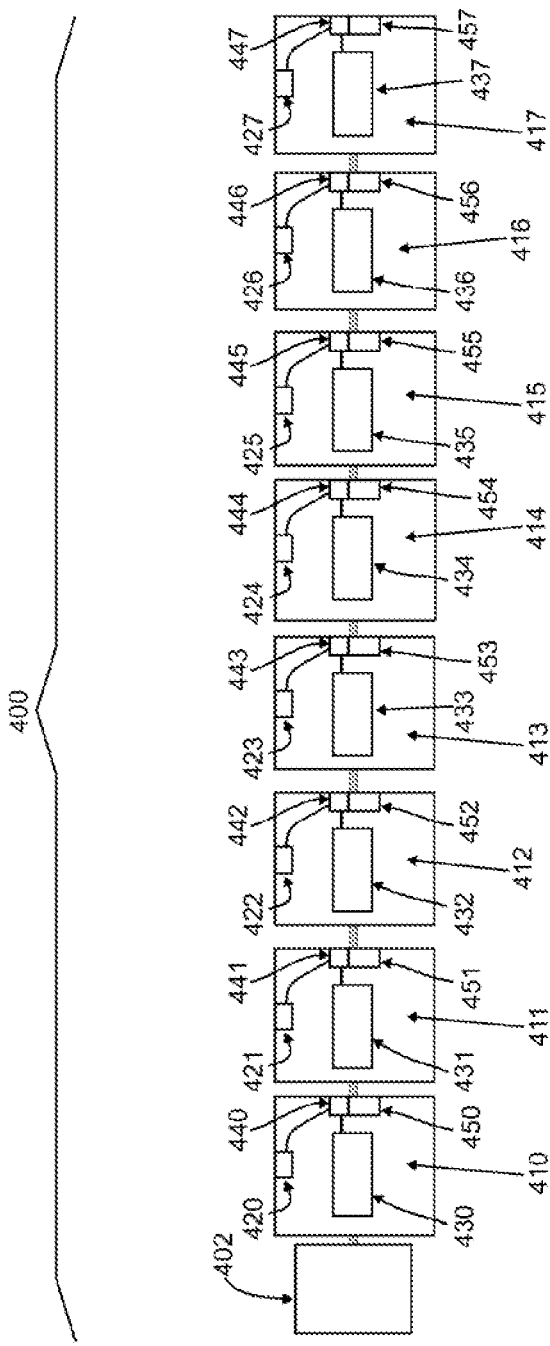
FIG. 4 represents yet another alternative embodiment of disinfection systems in a multi-car passenger rail trainset. This embodiment employs individually controlled systems in each car in a trainset.

An alternative embodiment to the one illustrated in FIG. 3 places a complete fog producing system in each car in a trainset. FIG. 4 illustrates a trainset 400 made up of a locomotive 402 with its associated passenger railcars 410-417. Matching configurations are comprised of local control system with communications and I/O devices attached 420-427, fog-dispersing equipment 430-437, pump modules 440-447, and disinfectant tanks 450-457. This arrangement provides maximum flexibility in the activation of fogging events. With smaller volume enclosures to fog, constituent components are correspondingly smaller than elements used to fog multiple spaces at a time. Each local control system 420-427 is individually activated by one of a locally recorded schedule, inputs to a rule-based engine, or manual input mechanism. The availability of each initiation method is at the discretion of the client when the system is defined. Each of these modes starts a timer that runs for a predetermined duration that is designed to match the disinfection needs of the space being treated for the specific disinfectant solution being employed. System software 148 shown in FIG. 1 provides grouping capabilities such that independent configurations installed in each railcar are able to carry out simultaneous operations if so defined by the managing authority.

Figure 5:
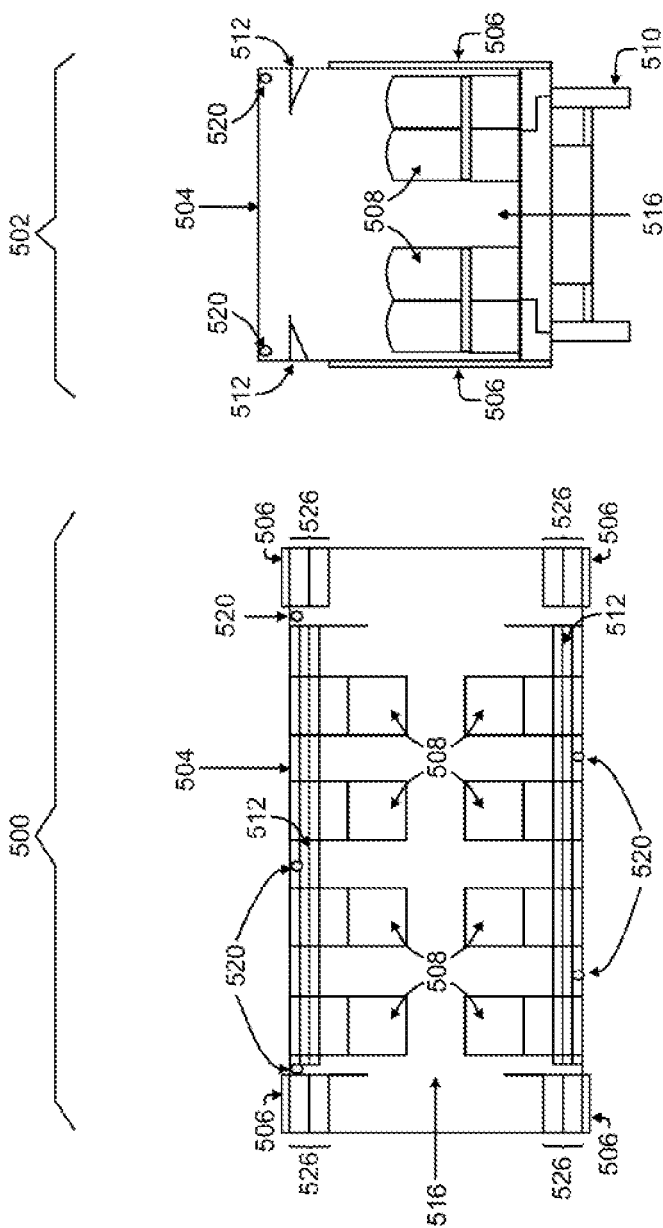
FIG. 5 depicts one example configuration of arrays of disinfectant fluid dispersal outlets that provide coverage within a single space, specifically a railcar.

Descriptions up to this point have focused on disinfectant fluid distribution, but there are also innovations for disinfection within the large volume enclosures themselves. Numerous topologies are consistent with the principles of the present application. Continuing with a mass transit embodiment for continuity of explanation, FIG. 5 provides one example configuration among many possible configurations. This configuration highlights distributions of disinfectant fluid dispersal outlets to provide coverage within a single railcar or vehicle. FIG. 5 includes a simplified top view 500 and a corresponding end view 502 for a representative passenger railcar to illustrate just one of many possible deployments of disinfectant fluid dispersal nozzles and outlets.

In top view 500 of FIG. 5, the body of a passenger railcar 504 has four doors 506 located near the ends of the vehicle for passenger entry and egress. Sets of seats 508 are adjacent to a central aisle 516. In the corresponding end view 502 of the same illustration, luggage racks 512 are ordinarily positioned above passenger seats 508. The railcar wheel assembly 510 is shown in end view 502 to help orient the viewer.

Referring again to top view 500 of FIG. 5, fluid dispersal nozzles 520 are placed above luggage racks 512 to propel disinfecting fog or mist over and through the racks and across the vehicle interior. Fluid dispersal nozzles 520 are composed of one or more types from a set of small orifice nozzles producing dry fog, larger orifice nozzles producing wet fog, and yet larger orifice nozzles producing mist particles. This combination allows fog to remain airborne, to move into small spaces around tray tables, and to fall on the racks, the seats, the vestibule areas, the floors, and any interior surfaces across from and near the nozzles. The selection of type and combination of nozzles is made to be most effective in dispersing fog or mist particles to counteract target pathogens in the enclosed volume.

Depending on nozzle type employed, fluid dispersal nozzles are effective when just placed along one side of the vehicle. However, this illustration shows a laterally alternating configuration for the purposes of illustrating at least one embodiment. A bilaterally symmetrical arrangement is effective depending on the internal vehicle components and air movement systems. Regardless of location, positioning of nozzles is designed to provide complete coverage of air spaces and surfaces within the interior of the vehicle enclosure. These upper fluid dispersal nozzles 520 are also shown in the end view 502. The positions shown are for illustration only and are non-limiting. Fluid pipes supplying these nozzles are not shown in these drawings and are preferably concealed in actual installations.

In some railcar designs, such as those with open areas under the seats, free air flow carries the disinfectant fog to the airspace and surfaces under the seats. However, a more complete or expeditious coverage option selectively involves the addition of lower disinfectant fluid nozzles (not shown in FIG. 5). An optional lower placement of disinfectant fluid dispersing nozzles provides effective disinfection under seats and in areas where peoples' shoes contact the floor. In practical application, such nozzles are placed appropriately to propel disinfectant fog into the step areas 526 near doors 506. Placement of such nozzles reduces the potential carriage of contagious agents into the vehicle that might be brought in on a passenger's shoes. It should be noted that the number and location of both upper fluid dispersal nozzles 520 and accompanying lower nozzles (not separately shown) or dispersal outlets are defined on an enclosure-by-enclosure basis in recognition of interior elements. Number and location also take into consideration objects and air movement within the enclosure. Further, enclosure owner preferences affect coverage and nozzle placements as well.

Figure 6:
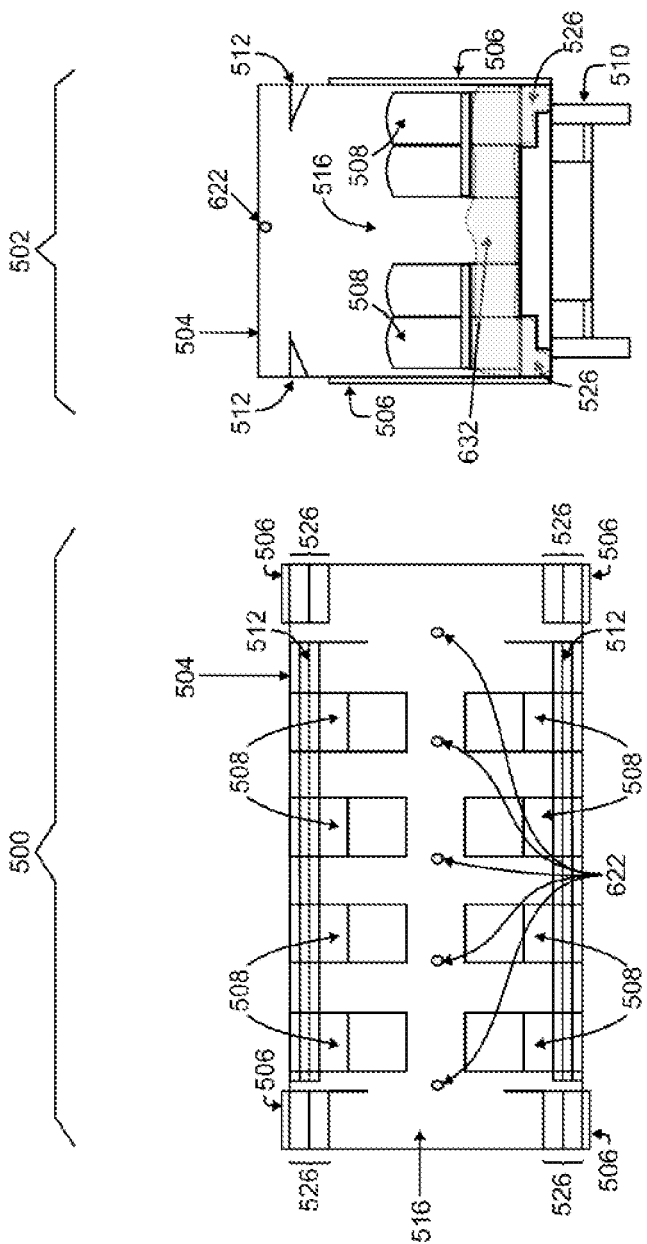
FIG. 6 depicts an alternative embodiment of a configuration of disinfectant fluid dispersal outlets that provide coverage within a single railcar.
Figure 7:
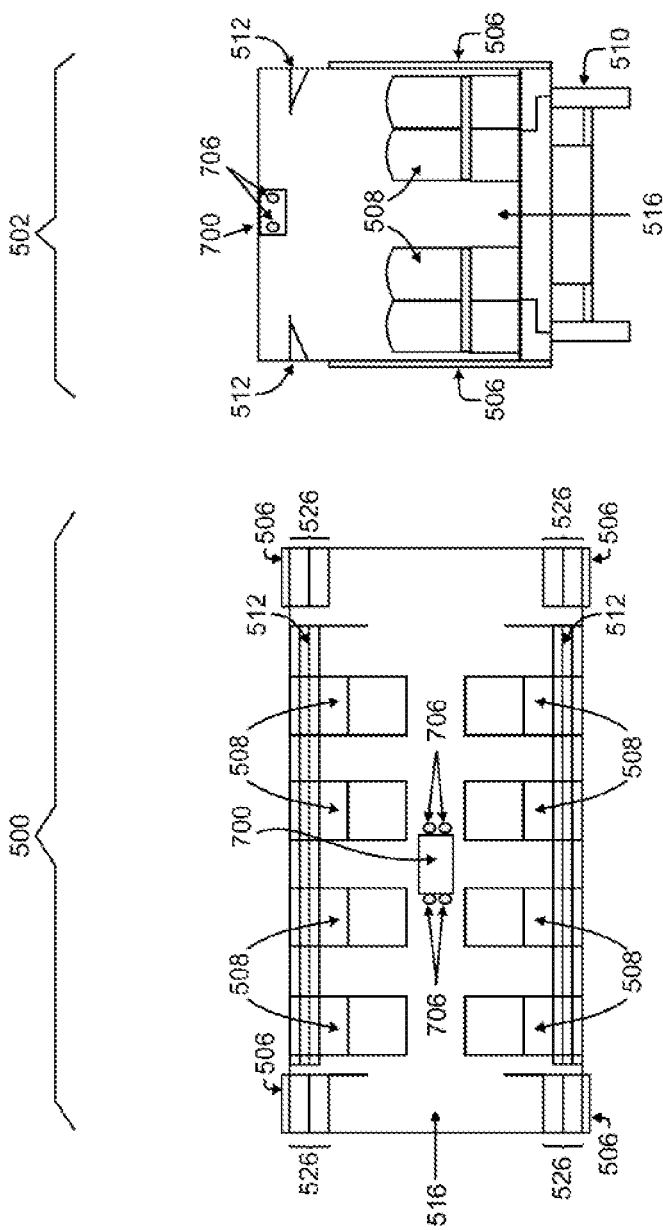
FIG. 7 illustrates yet another alternative embodiment of disinfectant fluid dispersal outlets housed in one or more centrally located devices that provide fog coverage within a single railcar.
Figure 8:
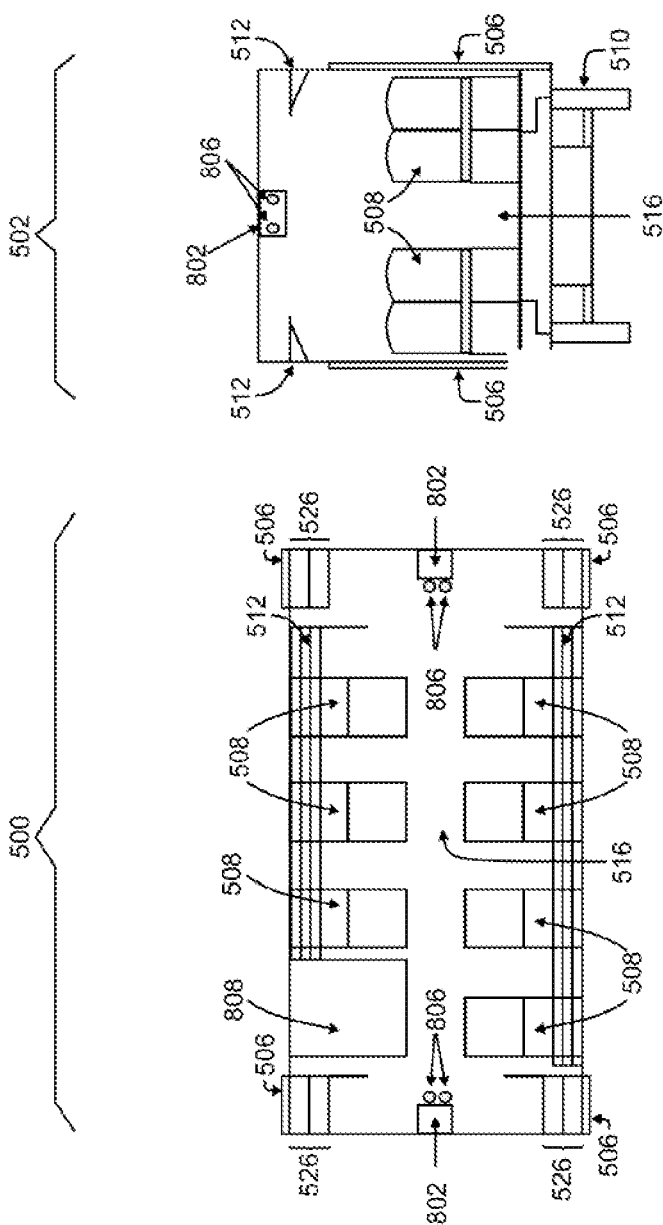
FIG. 8 illustrates still another alternative embodiment of disinfectant fluid dispersal outlets housed in one or more devices located at the ends of a single railcar.

Other embodiments also take into consideration interior elements and the movement of air and objects within an enclosure volume. FIGS. 6, 7 and 8 are three more alternative embodiments that are consistent with the principles of the present application. Adapting the drawing of the passenger railcar illustrated in FIG. 5, FIG. 6 shows placement of fluid dispersal nozzles and fogging outlets along the center line of the vehicle in the ceiling over the aisle. As defined previously, the body of an example passenger railcar 504 has four doors 506 located near the ends of the vehicle, seats 508 adjacent to a central aisle 516, luggage racks 512, and step areas 526. In the embodiment shown in FIG. 6, upper fluid dispersing nozzles and outlets 622 are placed in the ceiling above the walking aisle 516. Their dispersal patterns are defined through nozzle selection, pressure and other variables to provide coverage for airspace and surfaces in all directions around each nozzle 622. Dispersal patterns are also generated to cover the tops of luggage racks 512 as well. In this embodiment, a combination of dry fog and wet fog is produced for this application that is made heavier than air by formulation. In addition to falling on other surfaces, the resultant fog falls to the floor and forms a disinfectant cloud 632 at low levels that permeates cracks, flows into step areas 526, and builds to a level that envelops the undersides of seats. The small size of disinfectant fog particles is even effective at reaching the surfaces of raised/closed tray tables (not shown), if supplied on the vehicle. Cracks that have developed over time or that are artifacts of the manufacturing process also allow penetration of disinfectant fog particles into areas that may harbor infectious agents, improving the effectiveness of the sanitizing operation.

Large volume enclosures are designed for a variety of uses and constructed with assorted materials to serve their respective purposes. There are often reasons why certain configurations are advantageous over others due to a collection of factors and choices. In light of that fact and continuing with illustrations employing mass transit vehicles, FIG. 7 depicts yet another embodiment of a disinfecting system installation. This illustration builds on elements drawn in FIG. 5 for ease of understanding. In this embodiment, a single disinfectant dispersal unit 700 combines various nozzle and outlet types in one housing. Alternatively, two dispersal units that each dispense fog in primarily one direction are optionally mounted end-to-end or side-by-side near the middle of the railcar 500. The end-to-end and side-by-side topologies are not illustrated here as they are intuitively understood by description and located where a single housed unit is mounted. For this embodiment, a single dispersal unit 700 mounts on or above the ceiling in a central location in the vehicle. Fluid dispersal nozzles 706 produce mists, sprays and/or fogs that are carried by the inherent pressure of producing the fog or included or accessory air movement devices. Thus, fog and mist particles are carried to the ends of the vehicles from the central location. Some fluid dispersing nozzles or outlets 706 housed with this central unit generate fog that falls to the floor and travels throughout the vehicle, reaching floors and the undersides of seats, and in cracks and crevices. When the fog is falling, it is also effective at dispersing disinfectant solutions to the side inside walls and immediately adjacent seats. A disinfecting fluid reservoir or reservoirs are located according to descriptions for FIGS. 2-4. Reservoirs are positioned for convenience of maintenance and refilling in various alternative locations inside or outside the interior of the vehicle. Examples of potential placements include under the vehicle as previously suggested and on top of the vehicle. An above-vehicle placement requires a conveyance mechanism or hose arrangement (not shown) to refill easily. Such design decisions are made between system installers and enclosure owners according to unique circumstances of a given situation. One benefit of a centrally-located single dispersal unit or side-by-side/end-to-end units is the reduction in piping/tubing needed to transport disinfecting fluid throughout a car. An obvious drawback to distributed tubes and associated fittings is the inclusion of additional potential failure points. This is especially noteworthy in enclosures subject to frequent vibration and shock forces such as train cars and buses. A second benefit is found in simplified failure point determination. A single unit or side-by-side units have fewer parts and they are not distributed within the framework of a single vehicle or among multiple vehicles. A further additional benefit of a single unit is that replacement is much quicker with the capability to dismount just one item. A further benefit to a single unit or duplicate side-by-side units is that transit authorities save money by stocking and training to support only a single model. Installation on each vehicle of a given type in a fleet is identical, as well. Yet another benefit is production efficiency gained by a manufacturer who only needs to produce a single self-contained model, preferably lowering purchase price.

Yet another embodiment is illustrated in FIG. 8, in which two identical disinfecting system units 802 are employed, one at each end of an example railcar. Each unit includes fluid dispersal nozzles and outlets 806 for complete enclosure interior coverage. This configuration potentially reduces the overall dispersal time of disinfectant mists and fogs. It also has the benefit of concentrating disinfectants at the higher trafficked entry and exit portals 506 through selective pointing of a subset of nozzles. In vehicles that have a restroom 808, the closer proximity to a disinfection dispersal point improves the cleanliness of a space that is ordinarily less sanitary than other locations.

For the aforementioned various embodiments, there are usually many commercial reasons for installing a particular configuration of disinfecting components and systems. In addition, design of a given topology within a large volume enclosure is determined by several practical factors. One such factor is the density and viscosity of disinfectant fluids chosen. Another factor is the provision of disinfectant coverage of and around objects expected to exist within the enclosure. Yet another factor is the amount of time available for disinfection actions, which is important in several applications. Still another factor in topology design is for potential optional disinfectant concentration in chosen areas within the enclosure. Still other factors involve enclosure shape, aesthetics, and secondary air movement or HVAC devices, among other factors. Numerous such factors influence the configuration choices in an installation. These decisions are typically made by governing authorities or management for the subject establishment.

It is understood that discussions illustrated using passenger railcars are equally applicable to buses, automated people mover transport vehicles, streetcars, autonomous vehicles, and similar mobile conveyances. The similarities between passenger railcars and buses is evident to those familiar with mass transit vehicles, so embodiments employing either one or more disinfectant systems as depicted in FIGS. 5-8 are applicable to either enclosure type and the various vehicle types mentioned. Articulated buses use principles similar to embodiments depicted in FIGS. 2-4.

Figure 9:
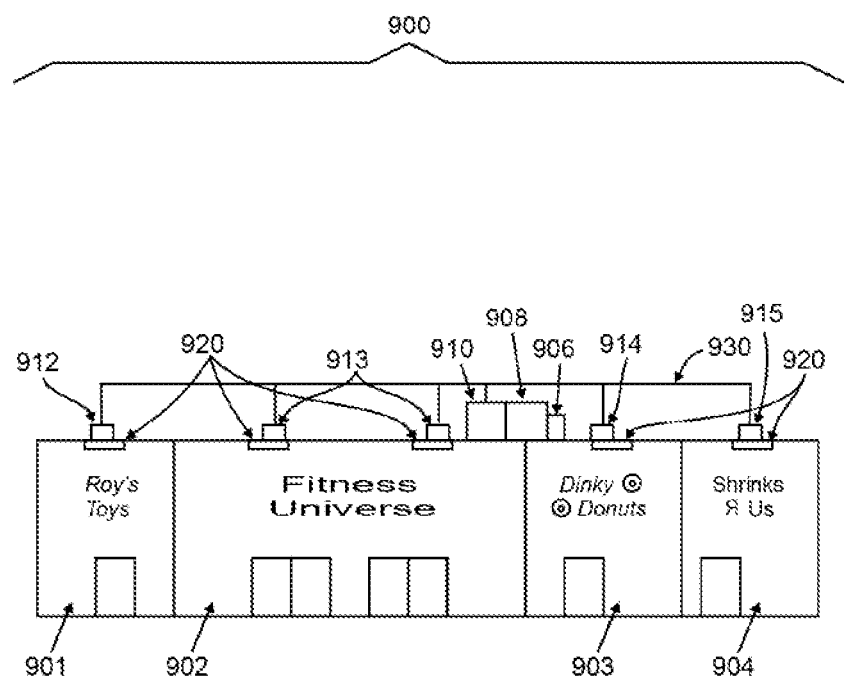
FIG. 9 is a drawing of a shared disinfecting system with individual controllers and dispersal systems applicable to collective business locations of retail and gathering spaces, such as those found in strip malls.

FIG. 2 techniques are also applicable to retail sales and gathering spaces, such as those located in strip malls, as diagrammed in FIG. 9. This figure portrays a front view of an example strip mall 900 comprised of retail spaces 901-904, each having its own separate internal space. In this embodiment, a single controller assembly subsystem 906 is housed in a weatherproof container and mounted securely on the roof of the strip in a central location above arbitrarily-selected retail space 903. The location above a specific store is not required, but an approximately central location is preferred in this embodiment. Located preferably near the controller is a disinfectant reservoir 908 (only one is shown) that supplies disinfecting fluid to the retail stores below. A disinfecting fluid pump module 910 is located next to or near the reservoir 908.

A common disinfectant fluid supply line 930 feeds disinfectant fluids to the corresponding retail or gathering spaces 901-904 through respective fluid control valves 912-915 located near the reservoir outlet. The amount of control valves for each retail space corresponds to the amount of nozzle and outlet arrays 920 located inside. Locations and amounts of arrays 920 are determined based on the size of the retail or gathering space, among other factors such as required disinfecting time and internal furnishings. Nozzle and fogging outlet arrays 920 are deployed on the ceilings of each retail space in this embodiment. It is understood that this deployment is for illustration only, and that other configurations are consistent with the principles of the present application. These arrays are each alternatively housed within single covers or deployed individually in various locations around the ceiling or elsewhere in each retail space. Although a single designation is used for arrays 920, each array will be different by corresponding to its own unique spatial requirements. Actuation of the pump module 910 is managed by the controller assembly subsystem 906 based on choices of either strip mall or individual store management. It is consistent with the principles of the present application to provide several alternative modes of activation, as described earlier. Examples include schedule initiation, inputs to rule-based engines, and manual controls. I/O devices are typically distributed to each retail space, providing inputs and outputs corresponding to each space to the controller 906. It is further consistent with this application to provide either collective or individual control of disinfection events in each retail space.

As discussed previously in the description of the example in FIG. 2, the system illustrated in FIG. 9 allows multiple control combinations among the stores through activation of the individual fluid control valves 912-915. Based on pump size defined for a given application environment and the potential provision for simultaneous operation, the system is sized to match the installed configuration. System capabilities include simultaneous disinfection actions among stores, individual disinfection operations, or combinations of stores being disinfected at one time based on circumstances. A previously identified example benefit of this capability is the freedom to selectively disinfect just one store if an infected person has entered it. In contrast, it is sometimes convenient for mall management, for example, to schedule all stores to be disinfected at one time in off-hours. As yet another example, if disinfecting fluid is temporarily running low in the centrally-located reservoir, a subset of the stores is optionally chosen for treatment at management's discretion. These and other benefits become apparent upon extended consideration.

Depending on the disinfecting fluid selected for the installation, an additional reservoir is employed to hold a second disinfectant fluid type. For example, a long-lasting surface disinfectant solution distributed as wet fog or spray is contained in one reservoir, while a dry fog-producing disinfectant solution is contained within another. Dry fogs are more effective in treating airborne pathogens. The number of reservoirs and types of solutions are not to be considered a limitation of the system or methodology. Correspondingly, when more than one reservoir is employed, additional fluid supply lines (not shown in FIG. 9) are employed.

Figure 10:
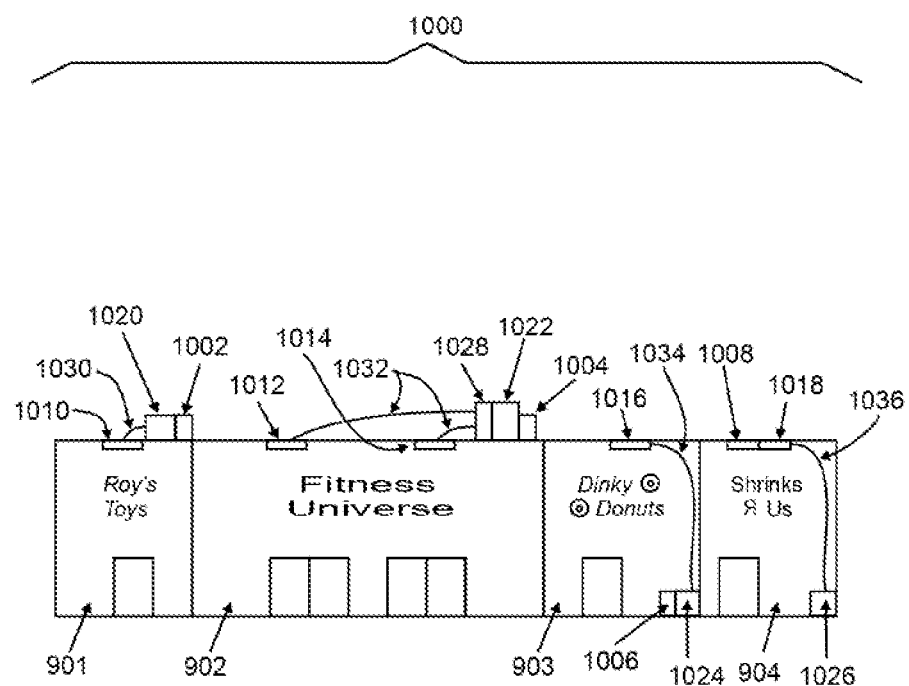
FIG. 10 depicts another embodiment for a collective business location deployment in which each space has its own independent disinfecting system.

Alternative embodiments are also appropriate for retail spaces and gathering locations. FIG. 10 depicts the strip mall 1000 similar to FIG. 9 with its separate retail businesses located in their own spaces 901-904. Instead of a single controller assembly subsystem and common disinfectant fluid reservoir, each retail space has its own disinfecting system. To illustrate the flexibility of implementations embodied in the principles of the present application, variations of installations are shown. Retail spaces 901 and 902 have their own respective controller assembly subsystems 1002 and 1004. Space 901 has a combined disinfectant fluid reservoir and pump module 1020 dedicated to its establishment. Due to the larger size in this illustration, space 902 has larger disinfectant fluid reservoir 1022 that is separate from its pump module 1028. The corresponding disinfectant dispersal nozzle and outlet arrays 1010 for space 901 are supplied through pipes 1030. Similarly, disinfectant dispersal nozzle and outlet arrays 1012 and 1014 are supplied through pipes 1032. Based on a large volume enclosure in this example, retail space 902 also has a selective fluid distributor 1028 incorporated with its pump module to accommodate flexibility for its large space. Each of these systems for spaces 901-904 feeds fluid dispersal nozzle and outlet arrays 1010-1018 that are deployed on the ceilings of their respective retail spaces. Decisions about disinfecting solution choices, frequency and duration of disinfection actions, and topology and locations of arrays are made by individual managers or owners to match their individual circumstances and preferences.

Continuing with the embodiment illustrated in FIG. 10, retail space 903 is shown with its controller assembly subsystem 1006 and combined disinfectant fluid reservoir and pump module 1024 housed within its interior space near ground level. Tubes 1034 for conveying disinfecting solution from reservoir 1024 supply the dispersal nozzle and outlet arrays 1016 that are deployed on the ceiling of space 903. Control of disinfection actions is local and under the discretion of store ownership or management. A different embodiment is shown for retail space 904, in which its reservoir/pump combination 1026 is located near ground level, and its controller assembly subsystem 1008 is co-located with a centrally-located nozzle and outlet array 1018 on the ceiling. Array 1018 is supplied through pipes 1036, similar to other stores. This arrangement is selectively beneficial for small retail or commercial spaces with few interior barriers. All the stores within this strip have independent control of disinfecting choices within their establishments. Various configurations of reservoirs, pumps, piping, nozzle arrays, and controllers are consistent with the principles of this application.

Figure 11:
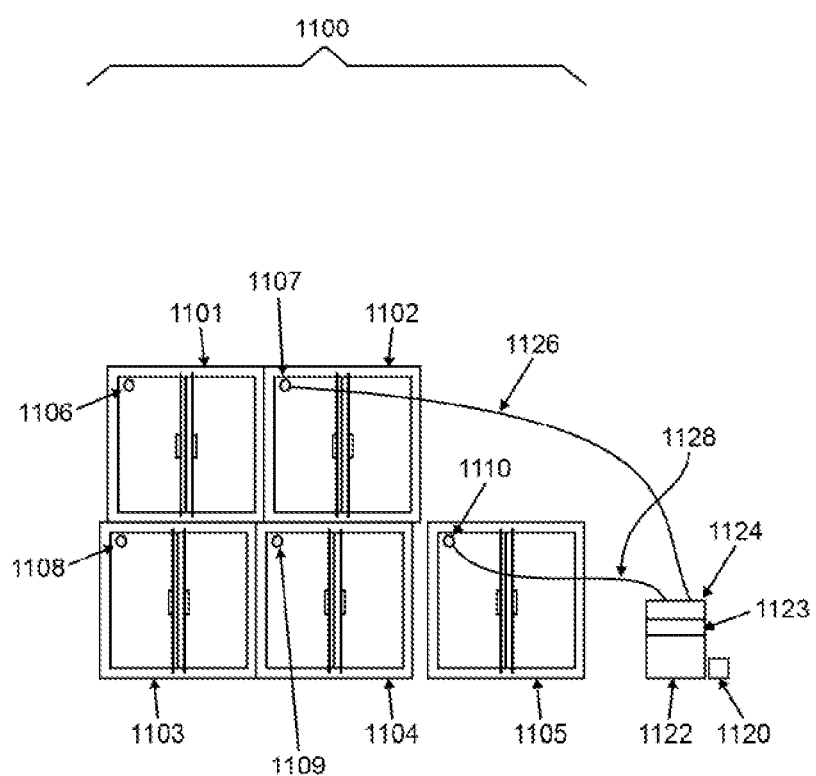
FIG. 11 illustrates an embodiment deployed in stacked cargo containers.

Shipping containers for cargo represent another type of large volume enclosure that is served effectively by the systems and method of the present application. FIG. 11 illustrates a collection 1100 of stacked containers 1101-1105 that are located in a storage yard, on a vessel, on an railcar suitable for transport, or other holding location. The nature of such containers is that they are designed for stacking in very close proximity on the top, bottom and sides. To satisfy this construction, disinfecting fluid connection ports 1106-1110 are located on the door sides of containers 1101-1105 respectively to allow reasonable access to supply fluids for nozzle arrays inside the containers. A single controller assembly subsystem 1120 preferably in a weatherproof housing manages the distribution of disinfecting solutions and fogs, mists or sprays from a central reservoir 1122. This embodiment includes a selective fluid distributor 1124 that is adjacent to the pump module 1123 and reservoir 1122. Alternatively, a common fluid supply hose (not drawn in this embodiment) supplies all the containers, and individual control valves (not shown) enable disinfection of individual containers. This is consistent with the method described and illustrated in FIG. 4. In the present embodiment drawn in FIG. 11, as an example, container 1102 is connected by flexible hose 1126 from container fluid connection port 1107 to selective fluid distributor 1124. Similarly, container 1105 is connected by hose 1128 at container fluid connection port 1110 to the selective fluid distributor 1124. Each container fluid connection port leads to nozzles and/or outlets (not shown here) located inside each container. These misting and fogging arrays are configured according to anticipated internal objects in topologies similar to those illustrated in FIGS. 5-8 or as might be otherwise designed following principles of the present application. Depending on anticipated or existing contents, one or more of mists, fogs or sprays are appropriate, and the container configuration is designed to accommodate owner decisions. Only two hose connections are shown, but the number of connections is not a limiting factor in the methods of the present application. FIG. 11 shows the disinfecting system controller, pump module and reservoir components as independent of the cargo containers. Various embodiments for these components or supply hoses, such as carried on a fork lift, suspended from a cargo crane, at a security checkpoint, or distributed from a pipe in a storage yard fluid supply system are consistent with the principles of this application. Various combinations of sequential or simultaneous disinfection events are also consistent with the principles of the present application.

Figure 12:
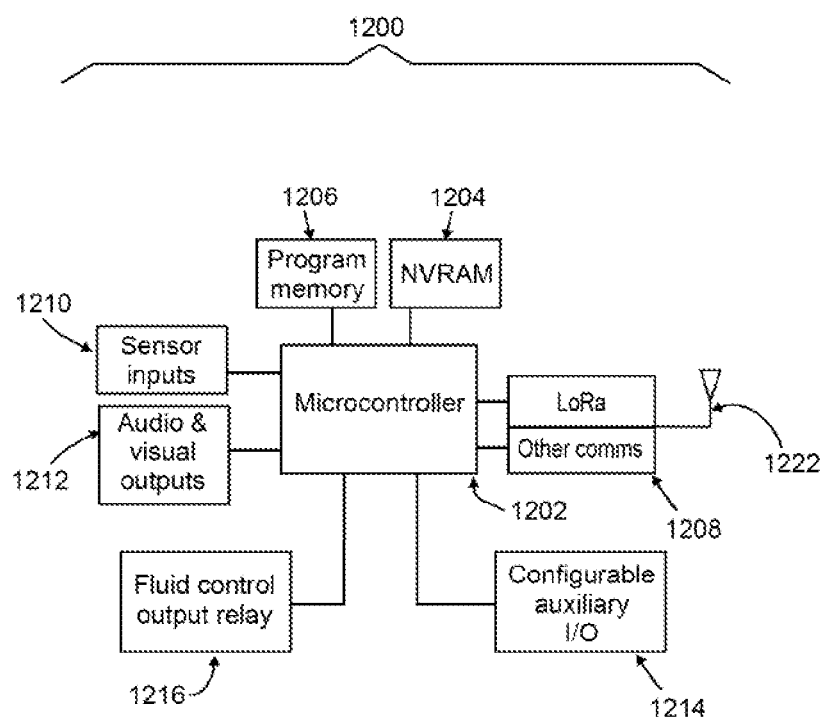
FIG. 12 is a high level generalized block diagram for one embodiment of a controller assembly.

FIG. 12 is a high level generalized block diagram for one embodiment of a controller assembly 1200. As implemented, it is housed in a suitable case that provides necessary protection for the environment of use. Furthermore, it is shock-mounted to protect against vibration damage and is shielded against EMI or RF interference, static electricity and other harmful forces. The block diagram shows just one embodiment of many different collections of components but includes sufficient parts to illustrate the functions described herein. This illustration is effective for initiation by schedule, by inputs to a rule-based engine, and by manual input. A microcontroller is not required for carrying out every embodiment of the present application. For example, timer functions are possible with a microcontroller, or they may alternatively be produced using other components. In addition, a microcontroller is not a requirement for some manual input initiated embodiments. For this embodiment, however, the heart of the system is a microcontroller 1202, selected to satisfy the needs of a given environment, and its corresponding NVRAM 1204 and program memory 1206. NVRAM is used in this illustration in recognition of unpowered states of some vehicle types at certain times. Other forms of electronic memory are alternatively acceptable. Data such as time and date of disinfection events and component failures are optionally stored in the NVRAM 1204. A communications subsection 1208 includes one or more RF-related components to provide LoRa, BLE, ZigBee, or some other suitable form of communications for transferring data, either unidirectionally or bidirectionally. Wired electronic communications means such as Ethernet provide alternatives where mobility is not a requirement. Wired solutions are not illustrated here. An embedded or external antenna 1222 is appropriate depending on the type of communications method. A GPS subsystem (not separately shown) is also selectively included. A sensor input subsection 1210 conditions signals from external sources for handling by the microprocessor. Non-limiting examples of some sensor inputs include sensors responsive to motion, disinfectant fluid reservoir level, RHT (relative humidity-temperature), system orientation, and external voltage supply level, among other potential sensor types. An assortment of audible and visual indicators is signified by block 1212. Such indicators optionally convey information about on/off state, power availability, sufficient fluid availability, optional fan operation, state of HVAC operation, fault conditions or other useful information that allows detection of operating states without physically entering an enclosure. These indicators are optimally placed where visually appropriate and most useful for sensing. Of significance is the configurable auxiliary I/O 1214, which allows for flexible selection of connections and future growth. Non-limiting examples of such auxiliary I/O include start/stop buttons, optional human-presence-detecting cameras, solid state relays for controlling air movement devices or HVAC fans, and status indicators distributed throughout the installation. Optional air movement devices or fans facilitate evaporation of disinfecting solutions on surfaces after an application. In addition, block 1216 devices manage relays for fluid control valves that support independent treatment of associated spaces.

Figure 13:
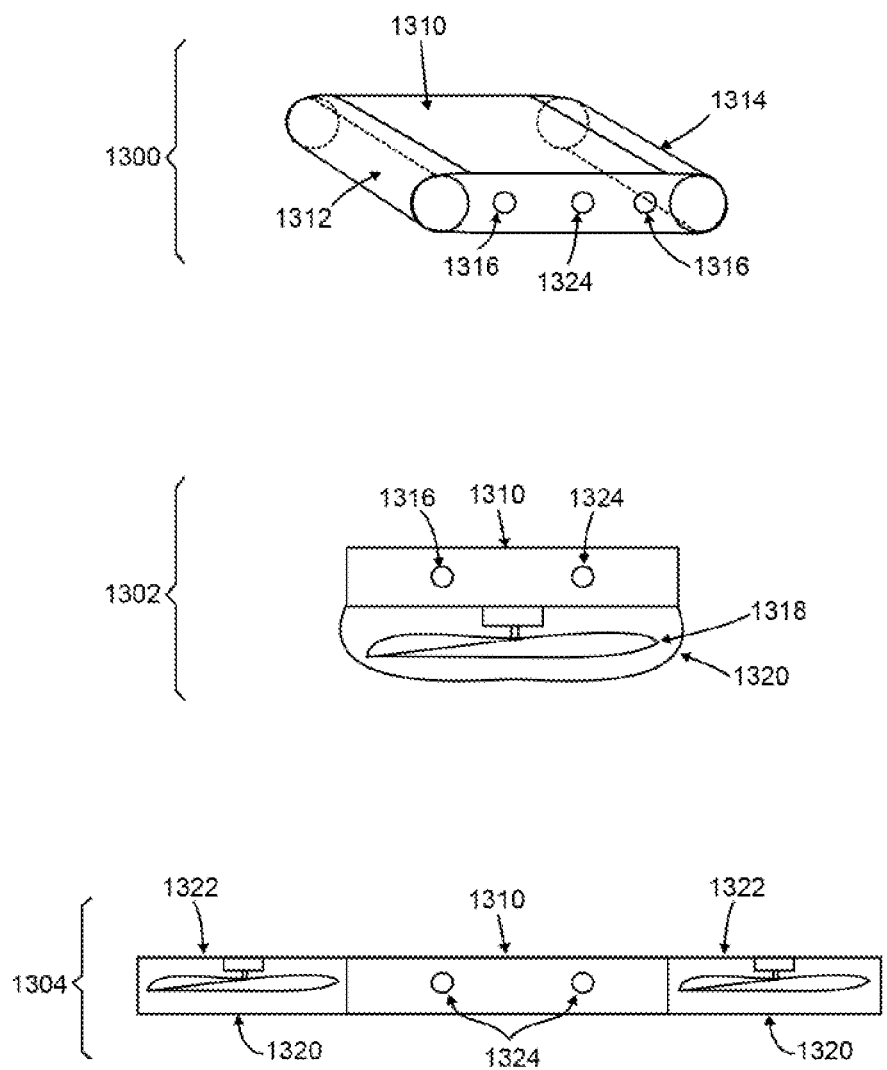
FIG. 13 illustrates 3 embodiments for a single-unit controller assembly and disinfectant dispersal system that also combines an air movement device for speeding up evaporation of disinfectant fluids after a disinfection event.

FIG. 13 illustrates 3 embodiments among many possible configurations for a single-unit controller assembly physically coupled with a disinfectant dispersal system that also combines an air movement device for speeding up evaporation of disinfectant fluids on surfaces after a disinfection event. Analogous to FIG. 7, in this embodiment, a consolidated disinfection assembly 1300 shown in perspective view combines differently sized nozzles 1316 and outlets 1324 (only one shown although more are selectively included) in one housing 1310 with a controller assembly (not shown), and the assembly is mounted on or above the ceiling in a central location in a large volume enclosure. Various combinations of nozzles and outlets are appropriate based on the target installation, types of fogs, mist and sprays required, and in keeping with the principles of the present application. Nozzles 1316 are designed to propel disinfectant fluid particles by high pressure to the ends and sides of the enclosure from the central location. Unit 1310 as illustrated shows a single unit, but side-by-side and end-to-end combinations are consistent with the principles of the present application. Tubular fan units 1312 and 1314 are shown selectively mounted on the sides of the consolidated disinfection assembly 1300. Hidden lines make the tubes easier to view but are not actually part of the construction. These fans move air within the large volume enclosure to speed up the evaporation process for a faster return to utilizing the space. Tubular fans moving air in the same direction establish a linear airflow that causes a specific circulation pattern in the enclosure. The choice of an air movement device of this type is based on the characteristics of the large volume enclosure and its contents. Alternative configurations of air movement devices are appropriate for other space topologies. A disinfecting fluid reservoir and pump module (not shown) are located separately from this placement and supply fluids to this unit through tubes or pipes. The reservoir is located at a place near the large volume enclosure that is convenient for maintenance and refilling. Placement decisions are made variously between architects, system installers and enclosure owners according to the unique circumstances of a given installation. As previously noted, one benefit of a consolidated centrally-located unit is the reduction in tubing needed to supply an array of nozzles and outlets otherwise distributed around the ceiling of the large volume enclosure. Tubes and associated fittings introduce additional potential failure points. A second benefit is maintainability of a consolidated unit. Replacement is much quicker with the capability to dismount a single unit or two conjoined units, and property owners or managers save money by stocking only a single model.

Continuing with FIG. 13, an alternative embodiment for a consolidated disinfection assembly 1302 is drawn in end view. In this configuration, the consolidated disinfection assembly 1302 combines variously sized nozzles 1316 and outlets 1324 (only one of each is shown although more are selectively included) in housing 1310 with a controller assembly inside and an air movement device 1318 underneath housing 1310. A screen or mesh-based safety cover 1320 allows free air movement when operating but protects passengers from possible contact with a blade when walking under the assembly. The entire assembly is preferably mounted on or slightly above the ceiling in a central location in the large volume enclosure. This air movement device establishes a different air circulation pattern than the tubular fans in assembly 1300 based on a vertical rotational axis, which is more appropriate for some enclosures or circumstances. As before, a disinfecting fluid reservoir (not shown) is located separately from this placement and supplies fluids to this unit from a pump module through tubes or pipes.

Further still in FIG. 13, yet another embodiment of a consolidated disinfection assembly is illustrated. In this incarnation, the consolidated disinfection assembly 1304 is composed of the controller/disinfectant dispersal means co-located in housing 1310 with a plurality of vertical axis air movement devices 1322 immediately adjacent. Fluid dispersing nozzles 1316 and outlets 1324 are placed in recognition of the locations of the associated air movement devices. As before, only a subset of nozzles and outlets is shown for illustration. Screen or mesh-based covers 1320 around each air movement device protect passengers from contacting the blades when walking under the assembly. In all embodiments 1300, 1302 and 1304, disinfecting actions and air circulation actions are selectively sequential, separated in time, or simultaneous to be most effective in a given circumstance.

Since disinfection of spaces is not intended to be interrupted, it's important that the amount of disinfectant fluid in the reservoir be known in order to maintain a sufficient supply. Accordingly, a level-sensing apparatus that provides an electrically-readable signal is therefore preferably associated with the reservoir or reservoirs. Numerous methods of accomplishing this are commercially available and suitable for incorporation depending on the target enclosure type and characteristics. Two examples of available technologies are linear Hall-effect arrays with an adjacent magnetic float and linear photosensor arrays with a parallel linear source of horizontally oriented light beams. Other examples include ultrasonic or radar level sensors and floats that rise or fall along a rod attached to a potentiometer.

Figure 14:
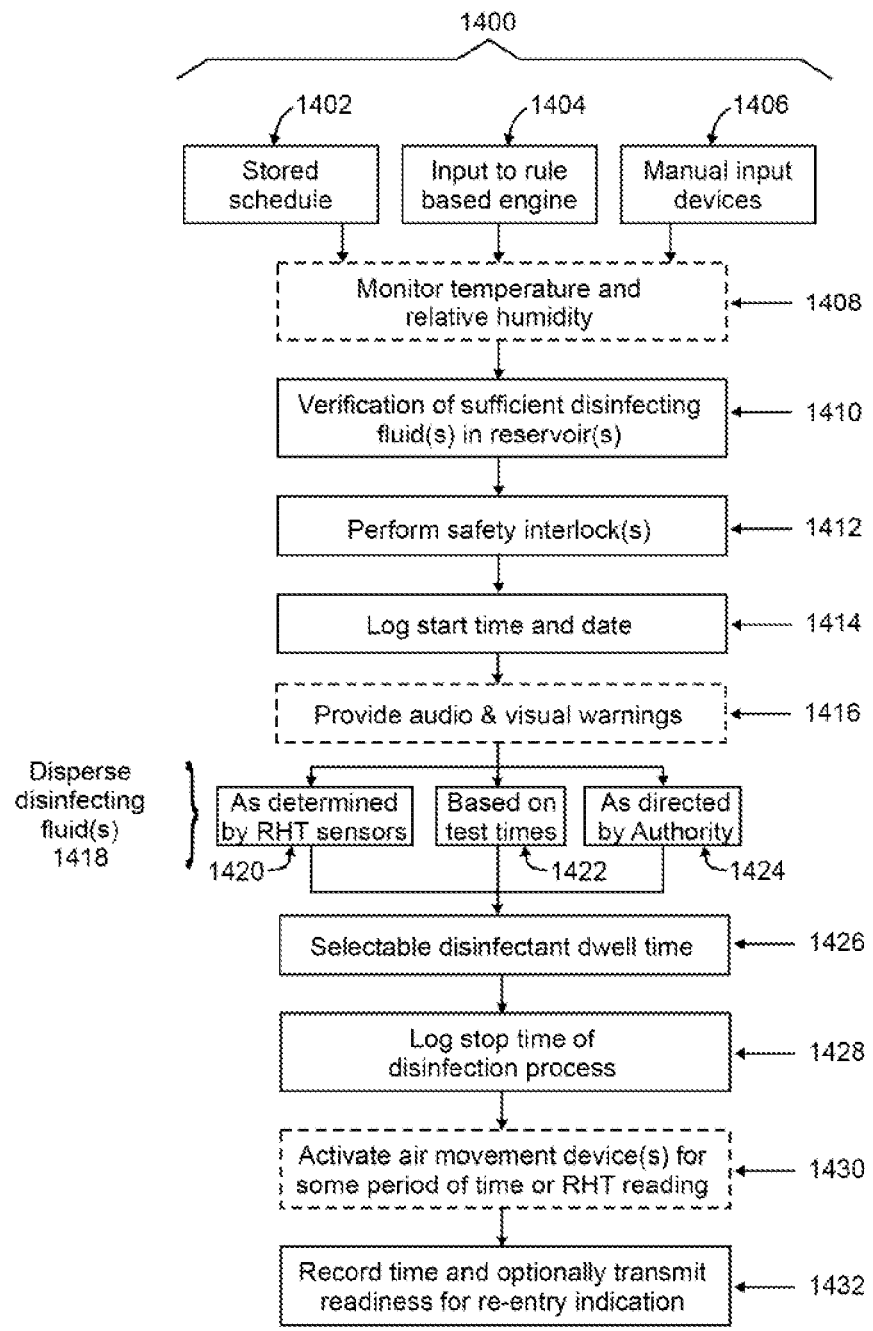
FIG. 14 portrays a sample series of steps in a representative disinfection sequence.

FIG. 14 portrays a sample series of steps in a representative disinfection sequence 1400. This illustration is one example of many possible sequences and is not meant to be limiting. Those skilled in the arts are able to define alternative sequences that are effective for their respective uses in a given environment. Optional steps in the sequence are shown as boxes with dashed lines, while routine steps are shown in boxes with solid lines. Initiation of a disinfection process is accomplished using one of at least three modes of initiation. A locally-stored schedule 1402 sends a signal to a programmable timer by reaching a predetermined time using a real-time clock with calendar and a stored schedule. Alternatively, a rule-based engine 1404 analyzes its assortment of inputs to make a determination that disinfection should begin. An affirmative output of the rule-based engine begins the programmable timer that controls pump module activation. Such a rule-based engine 1404 is also capable of preventing disinfection actions based on existing inputs. Examples of potential inputs include number of visits to the enclosure interior, occurrences of changes of enclosure contents, external weather conditions, and type of disinfectant fluid employed. Another alternative initiation method involves manual input devices 1406, such as switches that are engaged at will by the manager or staff attending the large volume enclosure. These input devices are also capable of initiating the start of the programmed time of disinfection. Transmitted signals sent through communications devices are selectively capable of directing the rule-based engine to begin fogging operations if the system is so programmed.

Continuing with FIG. 14, regardless of initiation source, the controller assembly optionally monitors the temperature and relative humidity 1408 on either a continuous or periodic basis depending on user preference and operational guidelines. Step 1410 is the verification of sufficient disinfecting fluid in one or more reservoirs. This is followed by one or more safety interlocks 1412 that ensure that no humans or animals are present in the enclosure, in the event that exposure to the disinfectant is to be avoided. An optional input from a conductor walk-through is another example of a safety interlock, albeit not automated. Steps to this point have determined that a disinfection event is allowed and that conditions for activation are appropriate and safe. Upon activation, the start date and time are preferably logged 1414 or transmitted to a base station computer at the beginning of the disinfection process. Additionally, audible and visual warnings 1416 are selectively provided if included in a given configuration.

Duration of dispersal of disinfecting fluids 1418 is selectively based upon conditions determined prior to activation. Non-limiting examples of conditions include relative humidity and temperature as sensed by RHT sensors 1420, pre-programmed time durations 1422 developed from previous tests for the specific type of enclosed space, or upon receipt of signals from the controlling authority 1424. Upon completion of the disinfectant dispersal, a dwell time 1426 occurs. The duration of the dwell time variously depends on the type of fluid used, conditions within an enclosure including existence of contents, type of infectious agents, or other determinants. At the completion of the dwell or evaporation time 1426, the stop time is logged 1428 at the controller assembly subsystem or in the software associated with the base station computer (not shown here). If an optional air movement apparatus is included and conditions are appropriate, the apparatus is activated 1430 to assist with evaporation of the disinfecting solutions. The period of operation for the air movement device is either preset or based on temperature and relative humidity readings. After this process has finished, the controller records the date and time and indicates in some fashion that the enclosure is ready for re-entry 1432. Such indications are one or more of changes in indicator lights, audible sounds, signals to external devices or the base station computer, or other means previously defined. Configured as required by a controlling authority, some or all of the steps included in this process are selectively transmitted to individuals or a command center (if one is part of the organizational structure) with selective information exchanges and optional approval messages according to the architecture of the system and service.

Figure 15:
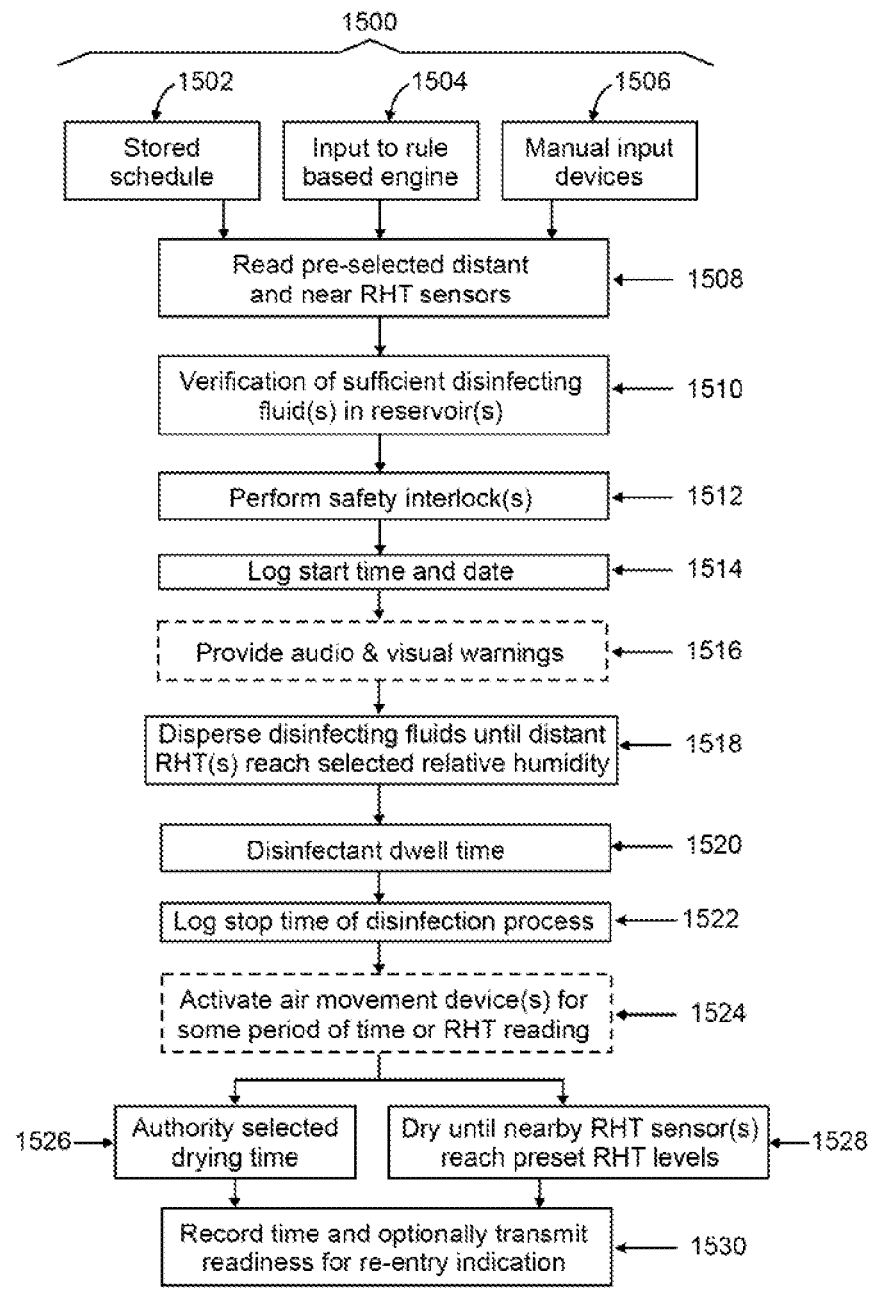
FIG. 15 illustrates another sample series of disinfection sequence steps with the timing of steps controlled by relative humidity and temperature readings from sensors distributed in key locations in a space being disinfected.
Figure 16:
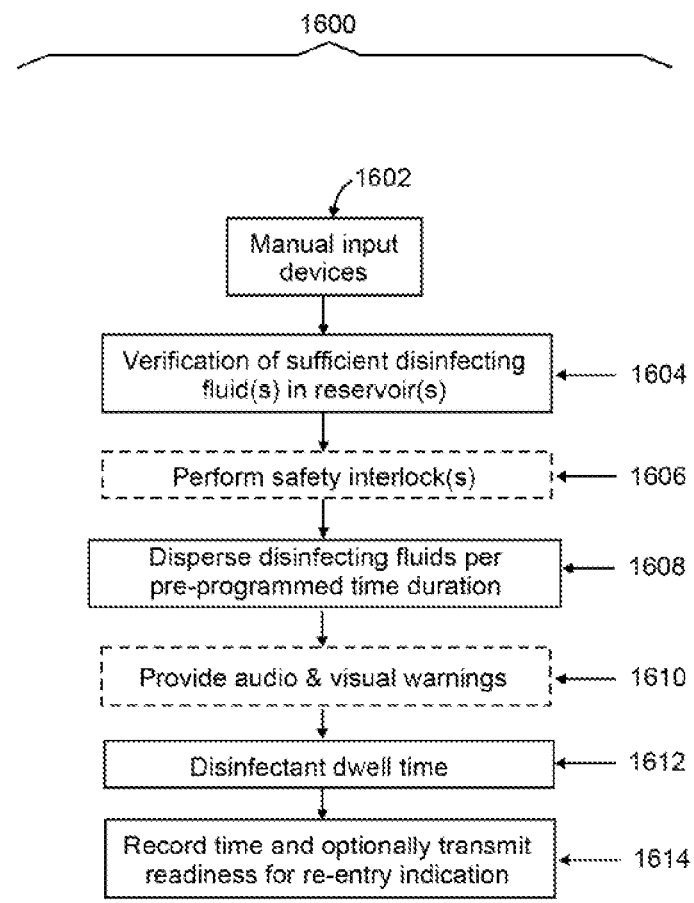
FIG. 16 shows yet another sample series of disinfection sequence steps initiated by a manual input device.
Figure 17:
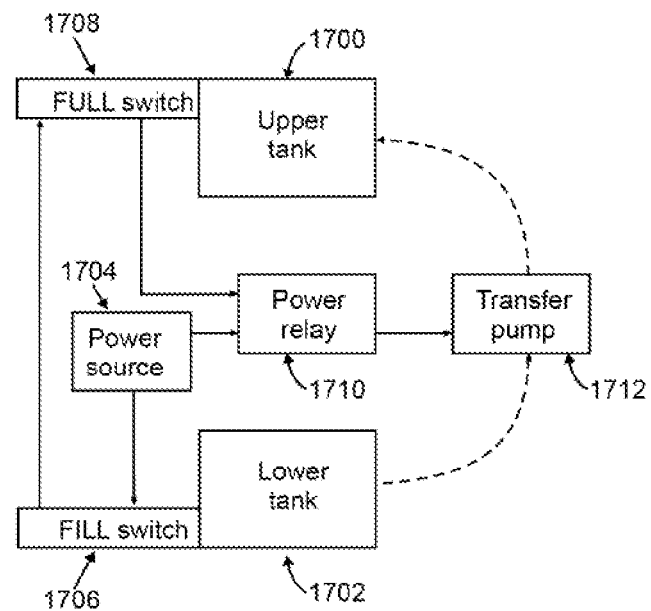
FIG. 17 illustrates one embodiment of an automated disinfection tank fluid transfer mechanism for use with the combination of a fluid-introduction or "fill" tank and a main disinfectant reservoir.

FIG. 15 portrays an alternative sample series of steps in a representative disinfection sequence 1500. This sequence particularly illustrates different readiness time durations based on either preset values or measurements from RHT sensors. This illustration is one example of many possible sequences and is not meant to be limiting. Those skilled in the arts are able to define alternative sequences that are effective for their respective uses in a given environment. As with FIG. 14, initiation of a disinfection process is accomplished using one of at least three devices or techniques. A locally-stored schedule 1502 sends a signal to a programmable timer by reaching a predetermined time using a real-time clock with calendar and a stored schedule. Alternatively, a rule-based engine 1504 analyzes its assortment of inputs to make a determination that disinfection should begin. An affirmative output of the rule-based engine begins the programmable timer that controls pump module activation. Such a rule-based engine 1504 is also capable of preventing disinfection actions based on existing inputs. Examples of potential inputs include number of visits to the enclosure interior, occurrences of changes of enclosure contents, external weather conditions, and type of disinfectant fluid employed. Another alternative initiation method involves manual input devices 1506, such as switches that are engaged at will by the manager or staff attending the large volume enclosure. These input devices are also capable of initiating the start of the programmed time of disinfection. Transmitted signals sent through communications devices are selectively capable of directing the rule-based engine to begin fogging operations if the system is so programmed.

Consistent with FIG. 14, regardless of initiation source, the controller assembly in FIG. 15 monitors the temperature and relative humidity 1508 on either a continuous or periodic basis depending on user preference or operational guidelines. Step 1510 is the verification of sufficient disinfecting fluid in one or more reservoirs. This is followed by one or more safety interlocks 1512 that ensure that no humans or animals are present in the enclosure, in the event that exposure to the disinfectant is to be avoided. An input from a conductor walk-through is another example of a safety interlock, albeit not automated. Steps to this point have determined that a disinfection event is allowed to occur and that conditions for activation are appropriate and safe. The start date and time are then logged 1514 as the optional audible and visual warnings 1516 are provided.

In FIG. 15, dispersal of disinfecting fluids 1518 is based upon relative humidity and temperature conditions measured during the course of disinfection. The system provides the means of controlling a starting and stopping of production of fog using readings from distributed relative humidity and temperature sensors to ensure desired disinfectant fluid dispersal results. The distributed relative humidity and temperature sensors also supply data to allow the controller assembly to determine sufficient evaporation of dispersed disinfectant fluid. In particular, RHT measurements are taken from sensors that are most distant from the fluid dispersal equipment. This method ensures complete coverage of the space with disinfecting fluid mists and fogs. Once the appropriate relative humidity level has been reached at the distant RHT sensor, the appropriate dwell time 1520 begins for a specific type of disinfectant fluid. Upon completion of the dwell time 1520, the stop time is logged 1522 at the controller assembly subsystem or base station computer software (not shown here). If an air movement apparatus is included and conditions are appropriate, the apparatus is activated to assist with evaporation of the disinfecting solutions (step not shown here). Whether an air movement device is included in the installed configuration or not is up to system designers, but this sequence is operative with or without step 1524. The period of drying is either preset 1526 as determined by the authority based on test results or determined by temperature and relative humidity readings 1528. If based on relative humidity sensing as in step 1528, the RHT sensor nearest the fluid dispersal equipment provides the comparison values. This sensor will have been exposed to the longest period of disinfection and is most likely to be the most saturated region. Thus, drying at this region of the space increases the likelihood that more remote regions that have received less disinfection fluid vapors and surfaces are already dry. This condition will have been validated through empirical testing for the given space. Finally, after this process has finished, the controller records the stop date and time and optionally transmits signals or activates indicators that the enclosure is ready for safe re-entry 1530. Configured as required by a controlling authority, some or all the steps included in this process are selectively transmitted to individuals, management authorities, or staff of a command or maintenance center (if one is part of a business structure) with selective information exchanges and optional approval messages according to the architecture of the system and service.

FIG. 16 illustrates a simplified disinfection initiation sequence 1600 using a manual input device 1602. Upon initiation by a suitable device, the level of disinfectant fluids available for use is checked in step 1604. Selected optional safety interlocks 1606 are performed next. If included safety interlocks are successfully passed, disinfectant fluid is dispersed in the enclosed volume according to a programmable timer with predetermined duration 1608. Optional audio and visual warnings 1610 are carried out prior to, during, and after the disinfection event according to protocols established for the client of interest. The disinfectant solution, whether in airborne form or precipitated onto surfaces, remains where it has been dispersed for a specific dwell time 1612 designed to effectively treat the target pathogens or conditions. A final step preferably includes recording the time of disinfection and activating an indicator or optionally transmitting an indication for safe re-entry 1614.

Certain configurations require placement of disinfection systems components in various positions. Some positions are preferred for effective operation but inconvenient for operations or maintenance. Examples of this circumstance are found in some vehicle models as well as roof-top mounted equipment in buildings. FIG. 17 illustrates one embodiment of an automated disinfection tank fluid transfer mechanism for use with the combination of a lower "fill" tank and a main disinfectant reservoir placed physically higher in an affected space. Signal and power lines are shown as solid lines, and fluid connections are shown as dotted lines. An upper tank 1700 is located in a physically higher elevation related to an enclosed space being disinfected. A lower tank 1702 is located at a lower elevation in a location that is more convenient for filling. The desired effect is for fluid to be transferred from the lower tank 1702 to the upper tank 1700 without manual intervention in the transfer process. To achieve this, a control signal passes through two switches to activate a power relay 1710 that powers a transfer pump 1712. One of these switches is a normally-open "fill" switch 1706, which is inserted into the lower tank 1702 at a low level such that the switch closes when fluid is introduced into the lower tank. The switch carries a voltage and current from a power source 1704. This power source supplies both a control voltage through the switches as well as power for a transfer pump 1712. The process begins when fluid is introduced to the lower tank. At this occurrence, fill switch 1706 closes and sends a signal to the normally-closed "full" switch 1708 mounted inside and near the top of the upper tank 1700. The full switch 1708 remains closed and conducts current until the level of disinfectant fluid in the upper tank reaches the top, where the switch is placed. When this condition occurs, the full switch opens and disconnects the control voltage to the power relay 1710, thus disconnecting power from the power source 1704 to the transfer pump 1712. When all fluid above the fill switch 1706 in the lower tank 1702 has been transferred to the upper tank, the fill switch opens up and interrupts power to the power relay 1710, turning off the pump 1712. Fluids may remain in the lower tank until the upper tank levels have dropped sufficiently to allow fluid transfers to resume.

The benefits of disinfectant tanks separately located from fill locations are readily apparent when considering the variety of configurations involving disinfecting equipment that is not located at ground level. Ground level is the most convenient location for the delivery of fluids to a disinfection system.

Non-Limiting Examples

The instant invention has been shown and described herein in what is considered to be the most practical and preferred embodiment. It is recognized, however, that departures may be made therefrom within the scope of the invention and that obvious modifications will occur to a person skilled in the art.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

I claim:

1. A disinfecting system comprising:
    an enclosed space with one or more doors for limited access by animals and humans and at least one controller for controlling operation of at least one pump;
    at least one reservoir for holding disinfection liquid;
    at least one manifold in fluid communications with the at least one pump and the reservoir, and the at least one manifold distributes the disinfection liquid, which the at least one pump has pressurized, to a set of one or more nozzles;
    whereby the at least one controller turns on the operation of the at least one pump to disperse disinfection liquid into the enclosed space based on one of at least three modes of initiation 1) a stored schedule, or 2) input to a rule-based engine, or 3) a manual input from an operator; and
    wherein input to a rule-based engine includes a geolocation system to provide a geographic position of the disinfecting system for operating the at least one pump in response to a definable position being satisfied.

2. The disinfecting system of claim 1, wherein input to a rule-based engine includes whether one or more safety interlocks are satisfied.

3. The disinfecting system of claim 1, wherein input to a rule-based engine includes whether one or more occupancy sensors indicates no presence of an animal or human in a defined area with the disinfecting system.

4. The disinfecting system of claim 1, wherein input to a rule-based engine includes whether one or more temperature and humidity sensors indicate a definable range.

5. The disinfecting system of claim 1, wherein input to a rule-based engine includes a verification of a sufficient amount of disinfecting liquid in the at least one reservoir.

6. The disinfecting system of claim 1 with at least one controller installed on a bus, a tram, a shipping container, a taxi, a van, a train, a subway, an automated people mover, an autonomous vehicle, a private mass-transit system, or a public mass-transit system, wherein at least a portion of the at least one controller controls disinfection of more than one defined area or car for the taxi, van, train, subway, automated people mover, autonomous vehicle, private mass-transit system or public mass-transit system.

7. The disinfecting system of claim 1, further comprising:
    at least one wireless network communicatively coupled between a portion of the at least one controller and a base station;
    wherein the portion of the at least one controller for controlling operation of the at least one pump is performed in response to exchanging control information with the base station over the at least one wireless network.

8. The disinfecting system of claim 1, further comprising:
    at least one valve for controlling distribution of the disinfection liquid to a first set of one or more nozzles, a second set of one or more nozzles or both, and the at least one valve is in fluid communications between the at least one manifold and one of the first set of one or more nozzles, the second set of one or more nozzles, or both; and
    at least one valve actuator communicatively coupled to the controller for opening and closing the at least one valve.

9. A disinfecting system comprising:
at least one controller for controlling operation of at least one pump;
at least one reservoir for holding disinfection liquid;
   at least one manifold in fluid communications to the at least one pump and the reservoir, and the manifold distributes the disinfection liquid, which the at least one pump has pressurized, to a set of one or more nozzles; and
   at least a first set of one or more humidity sensors positioned at a first distance from the set of nozzles in a predefined space;
   at least a second set of one or more humidity sensors positioned at a second distance from the set of nozzles, wherein the second distance is greater than the first distance in the predefined space;
   in response to a second definable humidity level that is above a second definable threshold as measured at the second set of one or more humidity sensors, the at least one controller controls the operation of the at least one pump to run; and
   in response to a first definable humidity level that is measured that is below a second definable threshold as measured at the first set of one or more humidity sensors, the at least one controller provides a notification that it is safe for animals or humans to enter the predefined space.

10. The disinfecting system of claim 9, whereby the at least one controller turns on the operation of the at least one pump based on one of at least three modes of initiation 1) a stored schedule, or 2) input to a rule-based engine, or 3) a manual input from an operator and wherein the rule-based engine includes a geolocation system to provide a geographic position of the disinfecting system and operating the at least one pump in response to a definable position being satisfied.

11. The disinfecting system of claim 10, wherein input to a rule-based engine includes whether one or more safety interlocks are satisfied.

12. The disinfecting system of claim 10, wherein input to a rule-based engine includes whether one or more occupancy sensors indicates no presence of an animal or human in a defined area with the disinfecting system.

13. The disinfecting system of claim 10, wherein input to a rule-based engine includes whether one or more temperature and humidity sensors indicate a definable range.

14. The disinfecting system of claim 10, wherein input to a rule-based engine includes a verification of a sufficient amount of disinfecting liquid in the at least one reservoir.

15. The disinfecting system of claim 10, with at least one controller installed on a bus, a tram, a shipping container, a taxi, a van, a train, a subway, an automated people mover, an autonomous vehicle, a private mass-transit system, or a public mass-transit system, wherein at least a portion of the at least one controller controls disinfection of more than one defined area or car for the taxi, van, train, subway, automated people mover, autonomous vehicle, private mass-transit system or public mass-transit system.

16. The disinfecting system of claim 10, further comprising:
   at least one wireless network communicatively coupled between a portion of the at least one controller and at least one set of remote control and command components; and
   wherein a portion of information for input to a rule-based engine utilizing the at least one controller for controlling operation of the at least one set of remote control and command components is transmitted over the at least one wireless network.

17. The disinfecting system of claim 16, further comprising:
   at least one valve for controlling distribution of disinfection liquid to a first set of one or more nozzles, a second set of one or more nozzles or both, and the at least one valve is in fluid communications between the at least one manifold and one of the first set of one or more nozzles, the second set of one or more nozzles, or both; and
   at least one valve actuator communicatively coupled to the controller for opening and closing the at least one valve.

18. The disinfecting system of claim 10, installed in one of a retail sales space, gathering space or a combination thereof, wherein a single controller assembly subsystem and disinfectant reservoir are housed in a central location to distribute disinfectant fluid to nozzles and fogging outlet arrays in the at least one of the retail sales spaces, the gathering spaces, or the combination thereof, through fluid control valves.

19. The disinfecting system of claim 10, installed in one of a retail sales space, gathering space or a combination thereof, wherein the at least one of the retail sales space, the gathering spaces, or the combination thereof has its own disinfecting system comprising a single controller assembly subsystem and disinfectant reservoir to distribute disinfectant fluid to nozzles and fogging outlet arrays in the at least one of the retail sales spaces, the gathering spaces, or the combination thereof.

* * * * *